United States Patent
Itsuji

(10) Patent No.: US 8,003,961 B2
(45) Date of Patent: Aug. 23, 2011

(54) ELECTROMAGNETIC WAVE GENERATING DEVICE, ELECTROMAGNETIC WAVE INTEGRATED DEVICE, AND ELECTROMAGNETIC WAVE DETECTOR

(75) Inventor: Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 500 days.

(21) Appl. No.: 12/326,037

(22) Filed: Dec. 1, 2008

(65) Prior Publication Data

US 2009/0146084 A1    Jun. 11, 2009

(30) Foreign Application Priority Data

Dec. 7, 2007    (JP) .................................. 2007-316807

(51) Int. Cl.
*G01N 21/35* (2006.01)
(52) U.S. Cl. .............. 250/504 R; 250/493.1; 250/503.1; 372/4
(58) Field of Classification Search ............... 250/493.1, 250/503.1, 504 R; 372/4
See application file for complete search history.

(56) References Cited

U.S. PATENT DOCUMENTS

| | | | |
|---|---|---|---|
| 7,248,995 | B2 | 7/2007 | Itsuji et al. |
| 7,723,708 | B2 * | 5/2010 | Ouchi et al. ............ 250/493.1 |
| 2005/0068116 | A1 | 3/2005 | Ham et al. |
| 2007/0235718 | A1 | 10/2007 | Kasai et al. |
| 2008/0315098 | A1 | 12/2008 | Itsuji |
| 2009/0009190 | A1 | 1/2009 | Itsuji |

FOREIGN PATENT DOCUMENTS

WO        2006/011668        2/2006

OTHER PUBLICATIONS

Heiliger, H. M., et al., Low-Dispersion Thin-M Microstrip Lines With Cyclotene (Benzocyclobutene) as Dielectric Medium, Applied Physics Letters, Apr. 28, 1997, vol. 70, pp. 2233-2235.
Dragonman, et al., "Terahertz Fields and Applications", Progress in Quantum Electronics, vol. 28, 2004, pp. 1-66.
PCT International Search Report and Written Opinion of the International Searching Authority, mailed May 12, 2009.
U.S. Appl. No. 12/359,225, filed Jan. 23, 2009, Takeaki Itsuji.

* cited by examiner

*Primary Examiner* — Michael Maskell
(74) *Attorney, Agent, or Firm* — Fitzpatrick, Cella, Harper & Scinto

(57) ABSTRACT

A transmission line for propagating a terahertz wave generated based on a carrier generated in a carrier generation layer includes a first region in which the terahertz wave propagates in a first direction and a second region having a different impedance compared to the first region and forming a reflection interface with respect to a terahertz wave which propagates opposite to the first direction. The transmission line is formed so that a distance from an irradiation location at which light is irradiated to the carrier generation layer to the reflection interface is smaller than D, where D is a distance converted from a half width of a time waveform of a terahertz wave which propagates in the first direction without passing through the reflection interface. Accordingly, a terahertz wave can be made to propagate with energetic efficiency, to a direction the terahertz wave is required to propagate.

12 Claims, 22 Drawing Sheets

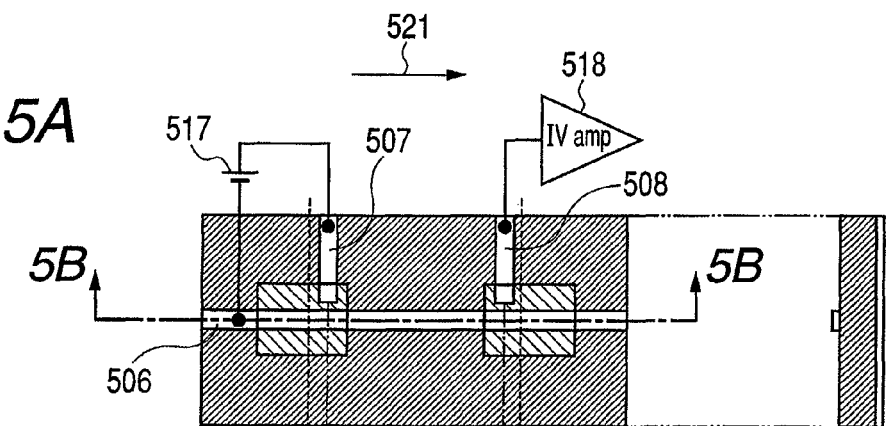
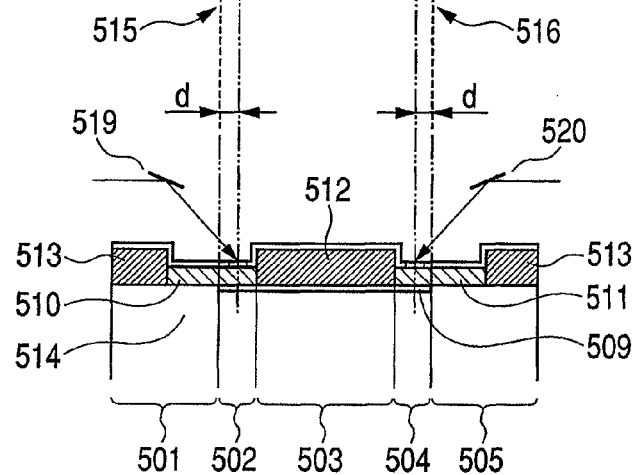
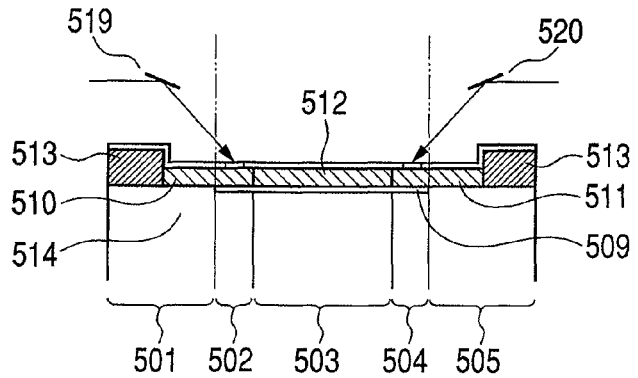

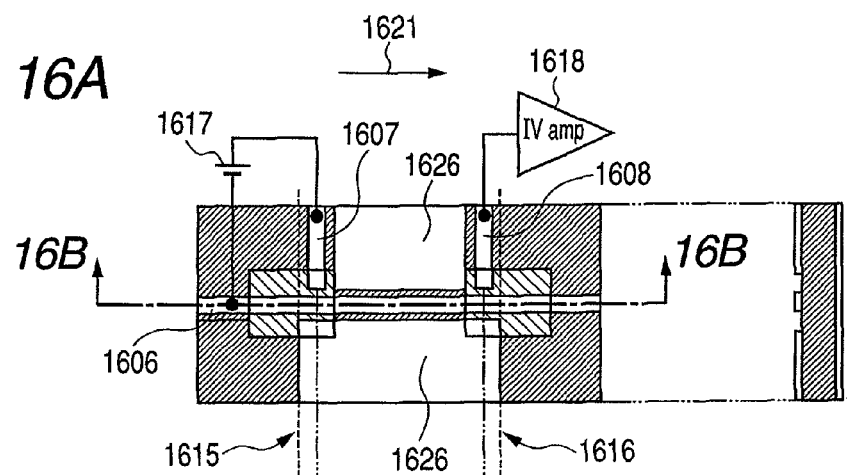
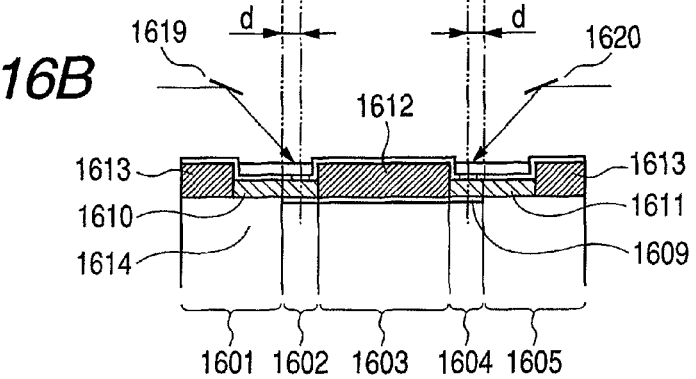

ELECTROMAGNETIC WAVE GENERATING DEVICE, ELECTROMAGNETIC WAVE INTEGRATED DEVICE, AND ELECTROMAGNETIC WAVE DETECTOR

BACKGROUND OF THE INVENTION

1. Field of the Invention

The present invention relates to an electromagnetic wave generating device. The present invention also relates to a device including an electromagnetic wave generating device and an electromagnetic wave detecting device integrated therein, and to an electromagnetic wave detector.

2. Description of the Related Art

In recent years, there has been developed an inspection technology for nondestructively analyzing and identifying a substance using an electromagnetic wave ranging from the millimeter wave band to the terahertz (THz) wave band (0.03 THz to 30 THz). A substance such as a biomolecule contains, due to its structure and state, an absorption spectrum in the terahertz wave band. The terahertz wave is safer than an X-ray, and hence it is expected to apply the terahertz wave to the imaging technology.

A technology of integrating a device for generating a terahertz wave and a device for detecting a terahertz wave on a transmission line is disclosed in Applied Physics Letters, vol. 70, p. 2233, 1997. FIG. 20 is a schematic view of the device disclosed in Applied Physics Letters, vol. 70, p. 2233, 1997, which is viewed from above.

The device illustrated in FIG. 20 includes a first electrode 2201, a second electrode 2202, a terahertz wave generating unit 2204, and a dielectric 2205. Voltage is applied to the first electrode 2201 and the second electrode 2202. An irradiation location 2203 is a location between the first electrode 2201 and the second electrode 2202 to which light is irradiated. By irradiating light to the irradiation location 2203, a terahertz wave is generated at the terahertz wave generating unit 2204.

The first electrode 2201 and the second electrode 2202 also serve as electrodes for propagating the terahertz wave. A terahertz wave generated at the terahertz wave generating unit 2204 is coupled to a transmission line including the electrodes, and thus the terahertz wave propagates through the transmission line.

In the case disclosed in Applied Physics Letters, vol. 70, p. 2233, 1997, the generated terahertz wave propagates mainly in two directions due to the structure of the device. That is, one terahertz wave is coupled to the first electrode 2201 to propagate in a first direction 2206, and another terahertz wave is coupled to the second electrode 2202 to propagate in a second direction 2207. In some cases, a terahertz wave required in an application of the device is only a component which propagates in the first direction 2206. In those cases, a terahertz wave which propagates in the second direction 2207 with respect to the generated terahertz wave is an energy loss, which is undesirable. When the terahertz wave is propagated in the first direction 2206 as much as possible, the energy of the generated terahertz wave can be used more effectively, which is efficient.

SUMMARY OF THE INVENTION

An electromagnetic wave generating device according to the present invention comprises:
a carrier generation layer for generating a carrier by light irradiation;
a first electrode provided on a first surface of the carrier generation layer for applying voltage to the carrier generation layer;
a reference electrode provided on a second surface opposed to the first surface of the carrier generation layer for defining a reference potential of the first electrode; and
a transmission line for propagating a terahertz wave generated based on the carrier generated in the carrier generation layer, the transmission line being formed so as to include the first electrode, wherein:
the transmission line includes:
  a first region in which the terahertz wave propagates in a first direction; and
  a second region having an impedance different from an impedance of the first region and forming a reflection interface with respect to a terahertz wave which propagates in a direction opposite to the first direction; and
a distance from an irradiation location at which light is irradiated to the carrier generation layer to the reflection interface is set to be smaller than D, where D is a distance converted from a half width of a time waveform of a terahertz wave which propagates in the first direction without passing through the reflection interface.

Further, another electromagnetic wave generating device according to the present invention comprises:
a carrier generation layer for generating a carrier by light irradiation;
a first electrode provided on the carrier generation layer for applying voltage to the carrier generation layer;
a reference electrode provided on the carrier generation layer for defining a reference potential of the first electrode; and
a transmission line for propagating a terahertz wave generated based on the carrier generated in the carrier generation layer, the transmission line being formed so as to include the first electrode, wherein:
the transmission line includes:
  a first region in which the terahertz wave propagates in a first direction; and
  a second region having an impedance different from an impedance of the first region and forming a reflection interface with respect to a terahertz wave which propagates in a direction opposite to the first direction; and
a distance from an irradiation location at which light is irradiated to the carrier generation layer to the reflection interface is set to be smaller than D, where D is a distance converted from a half width of a time waveform of the terahertz wave which propagates in the first direction without passing through the reflection interface.

Still further, another electromagnetic wave generating device according to the present invention comprises:
a carrier generation layer for generating a carrier by light irradiation;
a first electrode provided on a first surface of the carrier generation layer for applying voltage to the carrier generation layer;
a reference electrode provided on a second surface opposed to the first surface of the carrier generation layer for defining a reference potential of the first electrode; and
a transmission line for propagating a terahertz wave generated based on the carrier generated in the carrier generation layer, the transmission line being formed so as to include the first electrode, wherein:
the transmission line includes:

a first region in which the terahertz wave propagates in a first direction; and a second region having an impedance different from an impedance of the first region and forming a reflection interface with respect to a terahertz wave which propagates in a direction opposite to the first direction;

a distance from an irradiation location at which light is irradiated to the carrier generation layer to the reflection interface is set to be equal to or smaller than 0.5 D, where D is a distance converted from a half width of a time waveform of a terahertz wave which propagates in the first direction without passing through the reflection interface; and a refractive index of the first region is larger than a refractive index of the second region.

According to the present invention described above, an electromagnetic wave generating device capable of effectively using the energy of a generated terahertz wave can be provided.

Further features of the present invention will become apparent from the following description of exemplary embodiments with reference to the attached drawings.

BRIEF DESCRIPTION OF THE DRAWINGS

FIG. 1B is a schematic sectional view of the device taken along a line 1B-1B of FIG. 1A.

FIG. 2B is a schematic sectional view of the device taken along a line 2B-2B of FIG. 2A.

FIG. 4B is a schematic sectional view of the device taken along a line 4B-4B of FIG. 4A.

FIGS. 5A, 5B, and 5C are schematic views for describing an electromagnetic wave generating device of Example 1 of the present invention. FIG. 5B is a schematic sectional view of the device taken along a line 5B-5B of FIG. 5A. FIG. 5C illustrates a modification of the electromagnetic wave generating device illustrated in FIG. 5B.

FIG. 7B is a schematic sectional view of the device taken along a line 7B-7B of FIG. 7A.

FIG. 8B is a schematic sectional view of the device taken along a line 8B-8B of FIG. 8A. FIG. 8C is an enlarged schematic view of a region F of FIG. 8A.

FIG. 10B is a schematic sectional view of the device taken along a line 10B-10B of FIG. 10A. FIG. 10C is an enlarged schematic view of a modification of a region G of FIG. 10A.

FIG. 13B is a schematic sectional view of the device taken along a line 13B-13B of FIG. 13A.

FIG. 14B is a schematic sectional view of the device taken along a line 14B-14B of FIG. 14A.

FIG. 15B is a schematic sectional view of the device taken along a line 15B-15B of FIG. 15A.

FIGS. 16A and 16B are schematic views for describing still another modification of Example 1. FIG. 16B is a schematic sectional view of the device taken along a line 16B-16B of FIG. 16A.

FIG. 17B is a schematic sectional view of the device taken along a line 17B-17B of FIG. 17A.

FIG. 18B is a schematic sectional view of the device taken along a line 18B-18B of FIG. 18A.

FIG. 23B is a schematic sectional view of the device taken along a line 23B-23B of FIG. 23A.

FIG. 24B is a schematic sectional view of the device taken along a line 24B-24B of FIG. 24A.

DESCRIPTION OF THE EMBODIMENTS

First Embodiment: Electromagnetic Wave Generating Device

An electromagnetic wave generating device according to a first embodiment is now described with reference to FIGS. 1A and 1B. Here, the device according to this embodiment has a stripline structure, but the present invention is not limited thereto, and the device may have, for example, a coplanar waveguide structure.

Figure 1A:
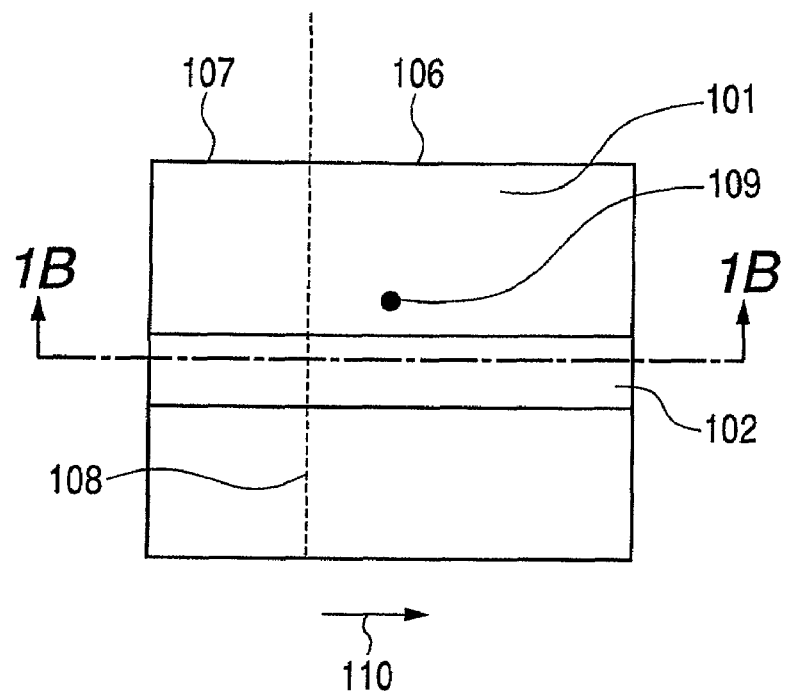
FIGS. 1A and 1B are schematic views for describing an electromagnetic wave generating device according to an embodiment of the present invention.

FIG. 1A is a schematic view of the device viewed from above. FIG. 1B is a schematic sectional view of the device taken along the line 1B-1B of FIG. 1A.

A carrier generation layer 101 generates a carrier by light irradiation. A semiconductor material such as gallium arsenide (GaAs) and indium gallium arsenide (InGaAs) may be used for the carrier generation layer 101. In the present invention, the material and the thickness of the carrier generation layer 101 are not specifically limited, and any material generating a carrier by light irradiation may be used.

A first electrode 102 is provided on a first surface 103 of the carrier generation layer 101 and applies voltage to the carrier generation layer 101. In the present invention, the material, the thickness, the size, and the like of the first electrode 102 are not specifically limited, and a known conductor may be used.

A reference electrode 105 is provided on a second surface 104 which is opposed to the first surface 103 of the carrier generation layer and defines a reference potential of the first electrode 102. In the present invention, the material, the thickness, the size, and the like of the reference electrode 105 are not specifically limited, and a known conductor may be used.

A transmission line for propagating a terahertz wave generated based on a carrier generated in the carrier generation layer 101 is formed to include the first electrode 102.

The transmission line includes a first region 106 and a second region 107.

The first region 106 is a region in which the terahertz wave propagates in a first direction 110.

The second region 107 is a region having an impedance which is different from an impedance of the first region 106 and forming a reflection interface 108 with respect to a terahertz wave which propagates in a direction opposite to the first direction 110.

It is assumed that a distance converted from a half width of a time waveform of a terahertz wave which propagates in the first direction 110 without passing through the reflection interface 108 as D. The transmission line is formed so that the distance from an irradiation location 109 at which light is irradiated to the carrier generation layer 101 to the reflection interface 108 is smaller than D. It should be noted that the above-mentioned distance D is converted from a half width and, in other words, can be said to be an effective distance in consideration of a refractive index distribution of the transmission line.

The irradiation location 109 at which light is irradiated to the carrier generation layer 101 is preferably a location at which a generated terahertz wave can be coupled to the first electrode 102.

In this embodiment, the transmission line for propagating a terahertz wave includes the carrier generation layer 101, the first electrode 102, and the reference electrode 105. In particular, the structure illustrated in FIGS. 1A and 1B is referred to as a microstripline structure.

(Other Structures)

With regard to the transmission line, other structures are also possible. For example, there can be employed a stripline structure in which a reference electrode is formed on the first surface 103 so as to be close to a side of the first electrode 102 with a certain space therebetween.

Figure 23A:
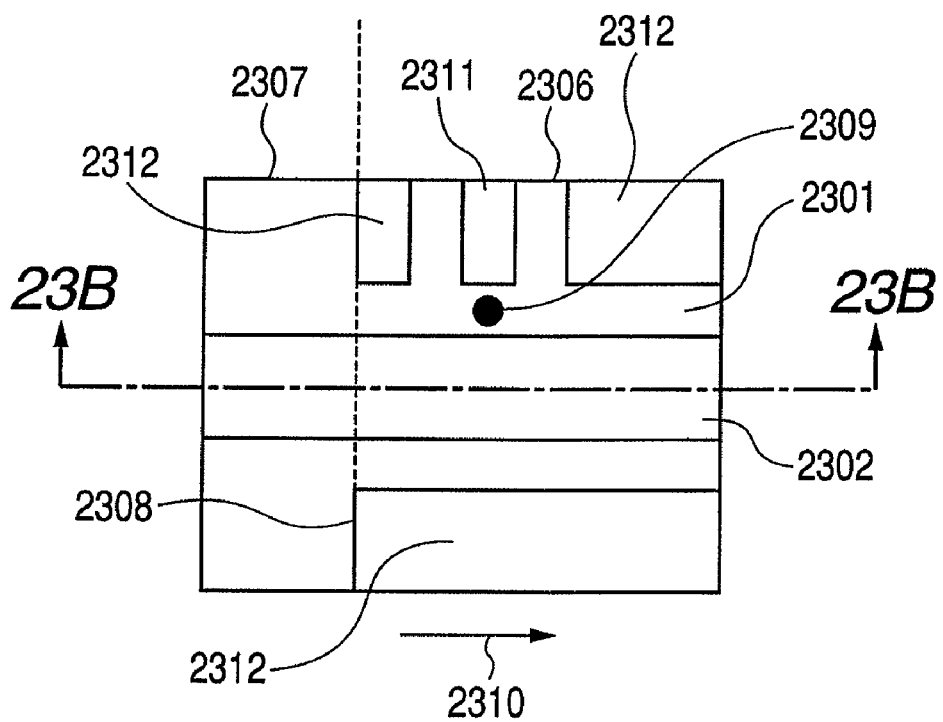
FIGS. 23A and 23B are schematic views for describing an electromagnetic wave generating device according to the embodiment of the present invention.
Figure 23B:
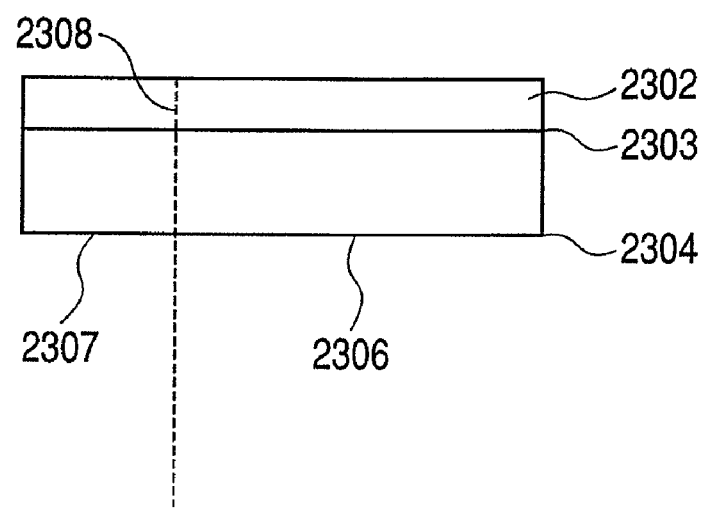

Further, as illustrated in FIGS. 23A and 23B, there can be employed a coplanar waveguide structure in which a reference electrode 2312 is formed so as to be close to both sides of a first electrode 2302 with a certain space therebetween. In the case of this structure, the reference electrode 2312 is provided on a first surface 2303.

Figure 24A:
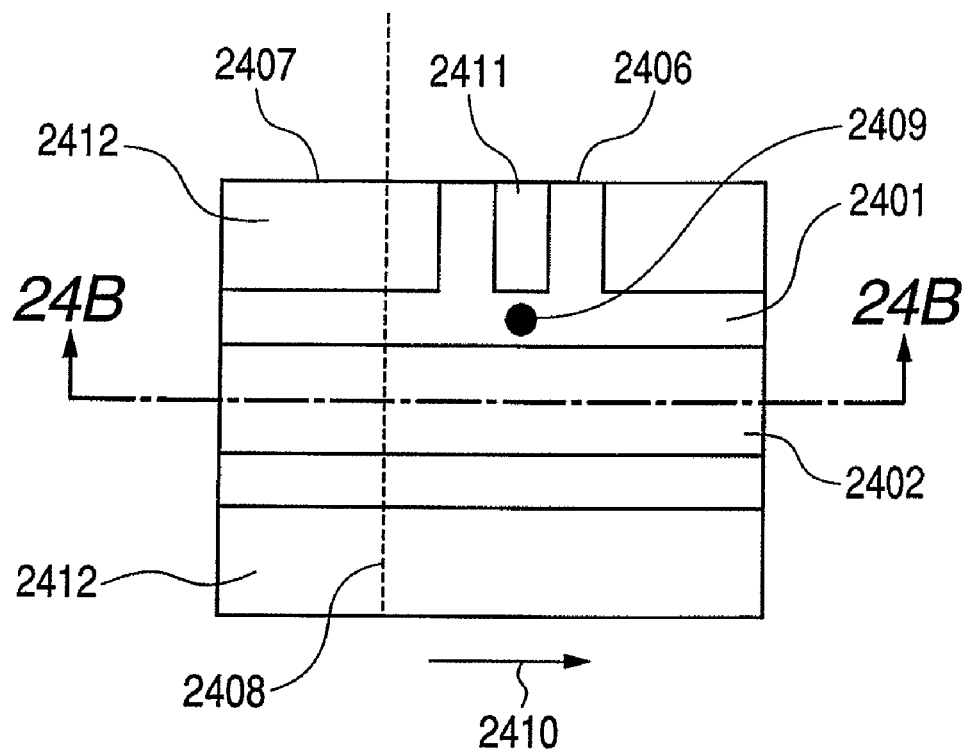
FIGS. 24A and 24B are schematic views for describing an electromagnetic wave generating device according to the embodiment of the present invention.
Figure 24B:
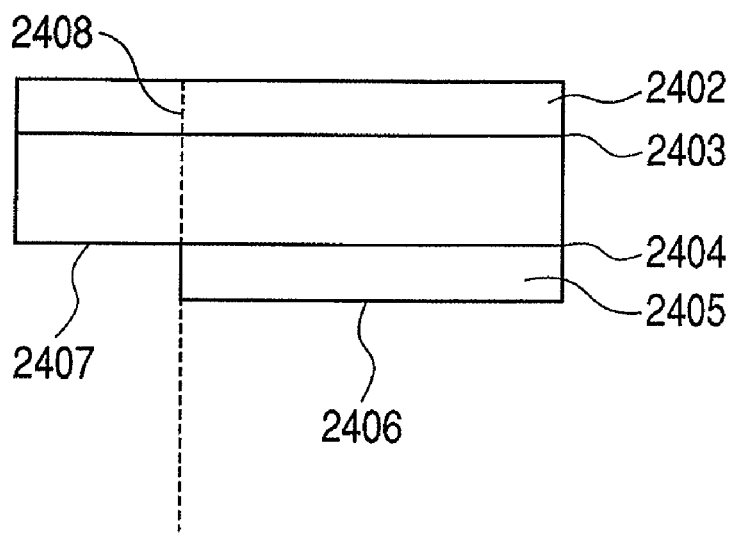

Further, as illustrated in FIGS. 24A and 24B, there can be employed a grounded coplanar waveguide structure in which a second reference electrode 2412 is formed so as to be close to both sides of a first electrode 2402 with a certain space therebetween (this structure is described in detail in Example 8). Still further, a single line structure which includes only the first electrode 102 may be used. It is essential only that voltage be applied to the carrier generation layer 101 and that a generated terahertz wave can be coupled to the transmission line. The structure of the transmission line can be appropriately selected according to the structure of the device to be used, the coupling of the device to an external system, and the propagation mode and the propagation characteristics of the terahertz wave.

(a) Reflection Interface

Next, a structure for providing the reflection interface is described.

(a-1) At Least One of End Portion of Reference Electrode and End Portion of First Electrode The reflection interface can be formed using at least one of an end portion of the reference electrode and an end portion of the first electrode.

Figure 1B:
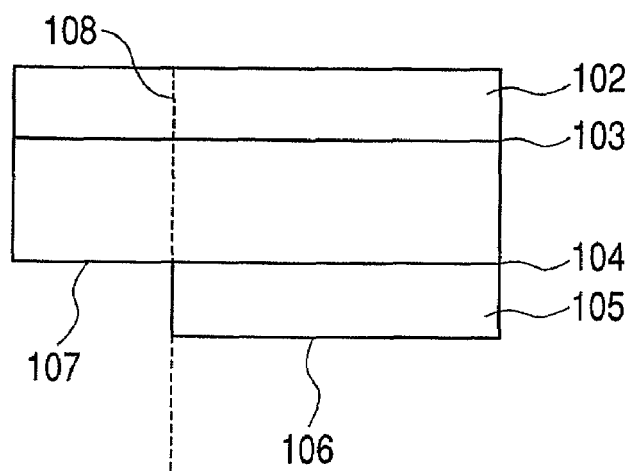

In FIGS. 1A and 1B, by providing an end of the reference electrode 105 at an interface between the first region 106 and the second region 107, the reflection interface 108 is formed. FIGS. 23A and 23B illustrate an exemplary structure of the reflection interface for a coplanar waveguide. As illustrated in FIGS. 23A and 23B, a reflection interface 2308 is formed by providing an end of the reference electrode 2312 at an interface between a first region 2306 and a second region 2307. It should be noted that reference numerals 2301, 2304, 2309, and 2310 denote a carrier generation layer, a second surface, an irradiation location, and the first direction, respectively. FIGS. 24A and 24B illustrate an exemplary structure of the reflection interface for a grounded coplanar waveguide. As illustrated in FIGS. 24A and 24B, a reflection interface 2408 is formed by providing an end of a reference electrode (first reference electrode 2405) provided on a second surface 2404 at an interface between a first region 2406 and a second region 2407. It should be noted that reference numerals 2401, 2409, and 2410 denote a carrier generation layer, an irradiation location, and the first direction, respectively. However, the structure of the reflection interface 108 is not limited thereto. The reflection interface may be provided by making the impedance of the first region different from the impedance of the second region.

Figure 2A:
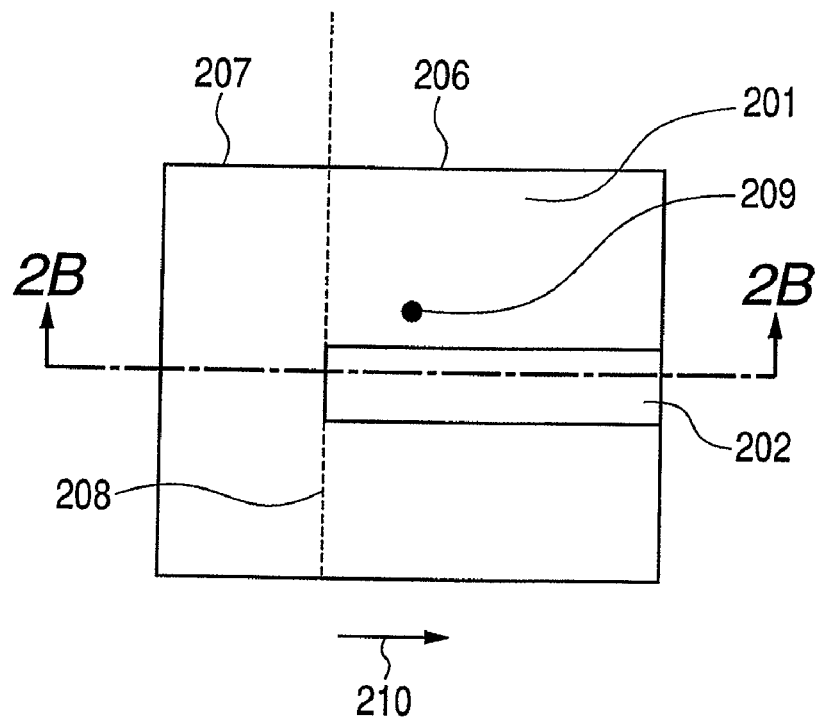
FIGS. 2A and 2B are schematic views for describing an electromagnetic wave generating device according to the embodiment of the present invention.
Figure 2B:
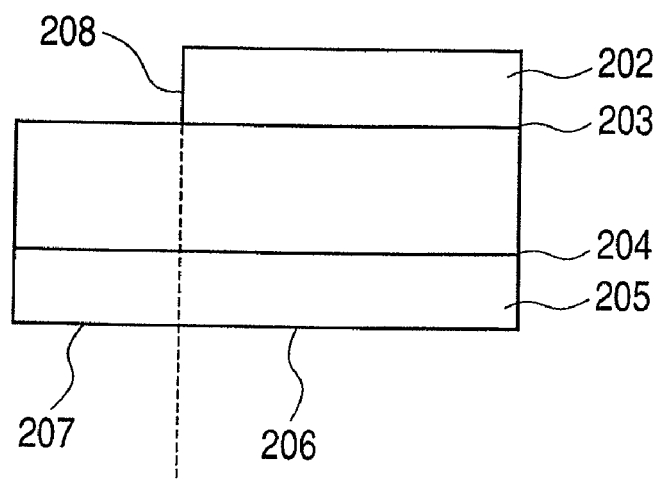

For example, the structure may be as illustrated in FIGS. 2A and 2B. FIG. 2A is a view of the device viewed from above, and FIG. 2B is a schematic sectional view of the device taken along the line 2B-2B of FIG. 2A. The structure illustrated in FIGS. 2A and 2B is different from that illustrated in FIGS. 1A and 1B in that a reflection interface 208 is formed by providing an end of a first electrode 202 at an interface between a first region 206 and a second region 207. It should be noted that, in FIGS. 2A and 2B, reference numerals 201, 203, 204, 205, 209, and 210 denote a carrier generation layer, a first surface, a second surface, a reference electrode, an irradiation location, and the first direction, respectively. This structure may be applied not only to the transmission line structure (stripline structure) illustrated in FIGS. 1A and 1B but also to other waveguide structures. For example, in the structure (coplanar waveguide structure) illustrated in FIGS. 23A and 23B or in the structure (grounded coplanar waveguide structure) illustrated in FIGS. 24A and 24B, the reflection interface can be formed by providing an end of the first electrode at an interface between the first region and the second region.

(a-2) Stub Electrode at First Electrode

The reflection interface can also be formed by providing a stub electrode at the first electrode.

The stub electrode is disposed at a location away from the reflection interface in a direction opposite to the first direction by ¼ of an effective wavelength of a terahertz wave which propagates in the direction opposite to the first direction. The length of the stub electrode is ¼ of the wavelength. The length and the location of the stub electrode are adjusted according to the wavelength of a terahertz wave which is required to be reflected.

The detail thereof is described in Example 2.

(a-3) Discontinuous Width of First Electrode: Stepped Electrode

The reflection interface can also be formed by making the width of the first electrode discontinuous.

The detail thereof is described in Example 3.

(a-4) Discontinuous Distance Between Reference Electrode and First Electrode

The reflection interface can also be formed by making the distance between the reference electrode and the first electrode discontinuous at a location forming the reflection interface in the carrier generation layer.

The detail thereof is described in Example 4.

(a-5) Other than Electrode

A structure in which the impedance of the first region is different from the impedance of the second region is not limited to a structure using electrodes. For example, the reflection interface may be formed by making the material or the structure of a layer of the device different at the interface between the first region and the second region.

For example, the reflection interface can also be formed by providing in the carrier generation layer a material having a refractive index which is different from a refractive index of the carrier generation layer.

The detail thereof is described in Example 5.

(b) Distance D Converted from Half Width of Time Waveform

Next, a distance D converted from a half width of a time waveform of a terahertz wave which propagates in the first direction 110 without passing through the reflection interface 108 is described with reference to FIGS. 3A and 3B. It should be noted that the above-mentioned distance D can be said to be, in other words, an effective distance converted from a half width (product of a half width of a time waveform and a velocity of propagation of a terahertz wave). The velocity of propagation of a terahertz wave can be determined by dividing the velocity of light by the refractive index of a portion through which a terahertz wave propagates.

Figure 3A:
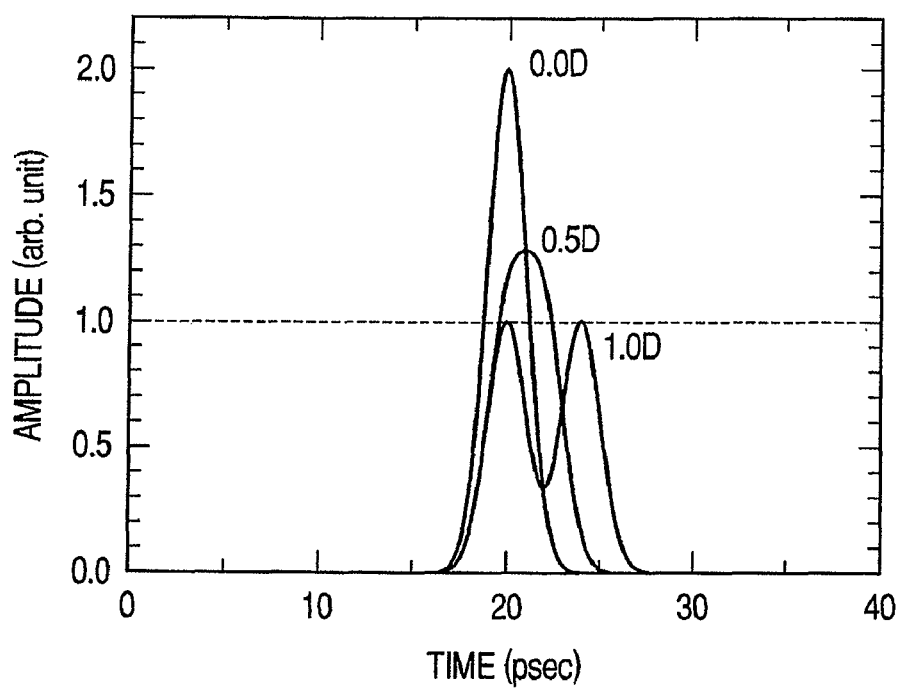
FIGS. 3A and 3B are graphs for describing a distance D converted from a half width of a terahertz waveform.
Figure 3B:
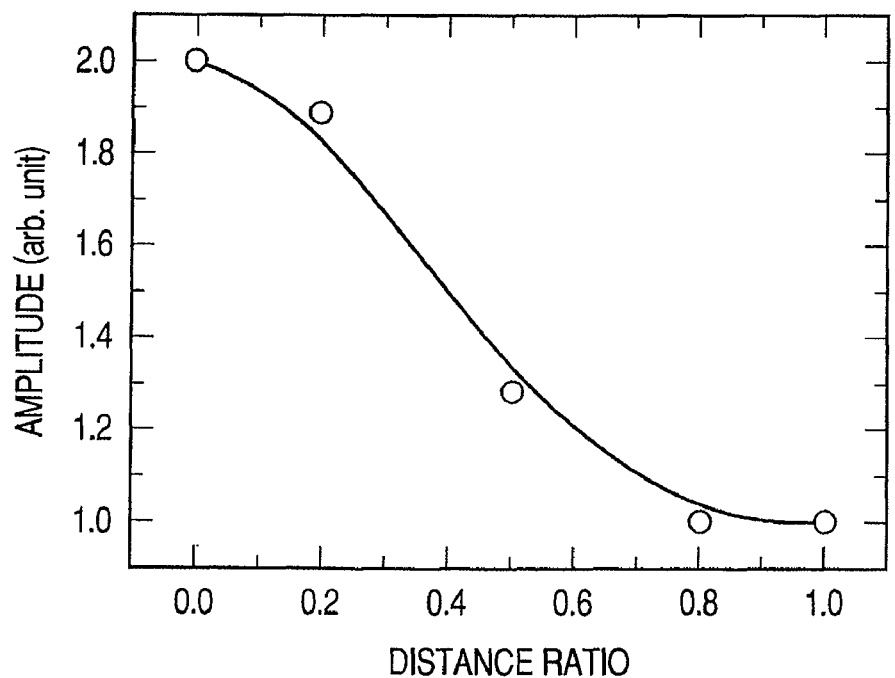

FIGS. 3A and 3B illustrates a change in waveform of a terahertz wave which propagates in the first direction 110 depending on the distance from the irradiation location 109 to the reflection interface 108 in the device structure as illustrated in FIGS. 1A and 1B.

Here, a terahertz wave generated based on a carrier generated in the carrier generation layer 101 is assumed to propagate in the following directions, that is, the first direction 110 without passing through the reflection interface 108 and the direction opposite to the first direction 110. Further, it is assumed that the intensity of the two terahertz waves which propagate in the above two directions are the same. Still further, a peak intensity of the terahertz wave which propagates in the first direction 110 without passing through the reflection interface 108 is assumed as 1, and a terahertz wave is assumed to be reflected by the reflection interface 108 without loss across the wavelength range of the terahertz wave.

FIG. 3A is a graph of time waveforms when the distance from the irradiation location 109 to the reflection interface 108 is 0.0 D, 0.5 D, and 1.0 D.

FIG. 3B is a graph in which an x-axis represents the ratio of the distance from the irradiation location 109 to the reflection interface 108 with respect to the distance D converted from the half width, and peak intensities of the terahertz wave with respect to the ratio are plotted.

From FIGS. 3A and 3B, the following can be seen as to a case where the distance from the irradiation location 109 to the reflection interface 108 is larger than D.

That is, a terahertz wave which propagates in the first direction 110 without passing through the reflection interface 108 and a terahertz wave which propagates in the direction opposite to the first direction 110 and is then reflected by the reflection interface 108 to propagate in the first direction are close to waves which are independent from each other.

Further, it can be seen that, when the distance from the irradiation location 109 to the reflection interface 108 is smaller than D, the intensity of a terahertz wave which propagates is increased. This is because the terahertz waves which propagate in the above-mentioned two directions overlap each other.

The distance from the irradiation location 109 to the reflection interface 108 is preferably 0.5 D or less, and more preferably, 0.0 D. The distance of 0.0 D means that the reflection interface is provided at the irradiation location. However, the present invention is not limited thereto.

It should be noted that, a half width of a time waveform of a terahertz wave varies depending on the device structure and the measurement conditions, and thus the effective distance also varies.

(c) Electrode to which Voltage is Applied

By irradiating light to the carrier generation layer, a carrier is generated. In order to generate a terahertz wave from the carrier, an electric field is applied to the carrier.

For example, in the device structure illustrated in FIGS. 1A and 1B, voltage is applied to the first electrode 102 and the reference electrode 105. This enables application of the electric field to the carrier generation layer 101.

Here, voltage is applied in the direction of film thickness of the device, whereby the intensity of the electric field applied to the transmission line can be controlled by controlling the film thickness of the device. When the film thickness is made to be smaller, because the distance between the electrodes is smaller, when the applied voltage is the same, the intensity of the electric field applied to the device becomes higher.

Figure 4A:
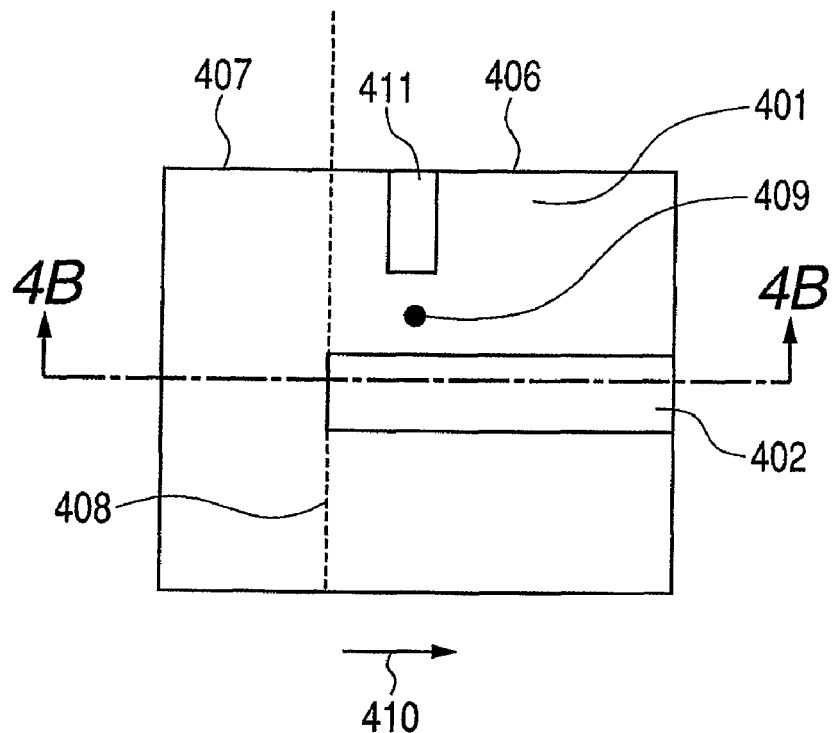
FIGS. 4A and 4B are schematic views for describing an electromagnetic wave generating device according to the embodiment of the present invention.
Figure 4B:
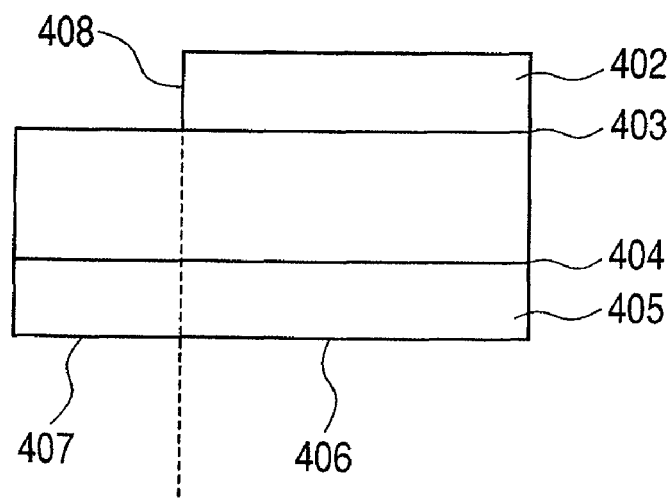

As illustrated in the schematic views of FIGS. 4A and 4B, the device is structured so that a second electrode 411 is provided on a first surface 403 of a carrier generation layer, and voltage is applied to a first electrode 402 and the second electrode 411. Here, an irradiation location 409 for light irradiation is between the first electrode 402 and the second electrode 411. The device illustrated in FIGS. 4A and 4B is quite different from the device illustrated in FIGS. 1A and 1B in that the second electrode 411 is additionally provided. It should be noted that, in FIGS. 4A and 4B, reference numerals 401, 404, 405, 406, 407, and 410 denote a carrier generation layer, a second surface, a reference electrode, a first region, a second region, and the first direction, respectively.

In a device structure illustrated in FIGS. 23A and 23B and a device structure illustrated in FIGS. 24A and 24B, a second electrode 2311 and a second electrode 2411 are provided on a first surface 2303 and a first surface 2403 of a carrier generation layer, respectively. As illustrated in FIGS. 23A and 23B, the second electrode 2311 is provided in the reference electrode 2312 with a certain space therebetween so as to be electrically insulated from the reference electrode 2312. Similarly, in the device structure illustrated in FIGS. 24A and 24B, a second electrode 2411 is provided in the second reference electrode 2412 with a certain space therebetween. Depending on the size of the space, the space may act as a reflection interface of a terahertz wave, but, by setting the size of the space to be, for example, a sufficiently smaller value compared with the distance D, the location of a reflected pulse is absorbed in a terahertz wave pulse which propagates, and the effect thereof can be alleviated. Preferably, the size of the space is set to be about 1/20 to 1/100 of an effective shortest wavelength of a terahertz wave which propagates. Then, it is difficult to recognize the space as a structure with respect to the terahertz wave, and thus, the effect can be further alleviated.

In the structure as illustrated in FIGS. 24A and 24B, it is also possible, as described above, to apply voltage to the first electrode 2402 and the first reference electrode 2405 without using the second electrode 2411.

(d) Terahertz Wave

Action until a terahertz wave is generated and propagates in the first direction when the electromagnetic wave generating device according to this embodiment is used is described with reference to FIGS. 1A and 1B. An electromagnetic wave device according to the present invention is applicable insofar as no contradiction arises.

First, by applying voltage to the first electrode 102 and the reference electrode 105, an electric field is applied to the carrier generation layer 101. Here, by irradiating light to the irradiation location 109, a generated carrier is accelerated by the electric field and a terahertz wave is generated. Light irradiated to the irradiation location 109 is preferably excitation light which corresponds to the absorption wavelength of the carrier.

The terahertz wave generated based on the carrier generated in the carrier generation layer 101 propagates through the transmission line. The transmission line is formed to include the first electrode 102 and includes the first region 106 and the second region 107.

In this case, the terahertz wave propagates mainly in two directions. That is, one terahertz wave propagates in the first direction 110 in the first region 106, and another terahertz wave propagates in the direction opposite to the first direction 110.

It is desirable that the first direction 110 be a direction which goes along the first electrode 102 as much as possible. This is because a terahertz wave generated based on a carrier generated in the carrier generation layer 101 propagates by being coupled to the first electrode 102.

In the electromagnetic wave generating device according to this embodiment, because the impedance of the second region 107 is different from the impedance of the first region 106, the reflection interface 108 is formed for a terahertz wave which propagates in the direction opposite to the first direction 110.

Here, it is assumed that a distance converted from a half width of a time waveform of a terahertz wave which propagates in the first direction 110 without passing through the reflection interface 108 is D. The transmission line is formed so that the distance, from the irradiation location 109 at which light is irradiated to the carrier generation layer 101, to the reflection interface 108, is smaller than D. For example, in the device illustrated in FIGS. 4A and 4B, a reflection interface 408 is formed so that the distance from the irradiation location 409 to a center line of the second electrode 411 which is perpendicular to the first electrode 402 is smaller than D.

The terahertz wave which propagates in the direction opposite to the first direction 110 is reflected by the reflection interface and overlaps the terahertz wave which propagates in the first direction 110. In this way, a terahertz wave is synthesized from the terahertz waves which propagate in the two directions and the intensity thereof becomes higher. As a result, the generated terahertz wave propagates efficiently in the first direction 110 in terms of energy.

Here, the above-mentioned reflection interface reflects terahertz waves in all the wavelength range, but the present invention is not limited thereto and may employ a structure in which a terahertz wave in a specific wavelength range is reflected.

(e) Refractive Index

In the electromagnetic wave generating device according to this embodiment, it is desirable that a refractive index of the first region 106 be larger than a refractive index of the second region 107. It should be noted that the refractive index can be said to be, in other words, an effective refractive index.

Therefore, the terahertz wave which propagates in the direction opposite to the first direction 110 can be reflected in the same phase. As a result, the terahertz wave which propagates in the first direction 110 and the terahertz wave which is reflected by the reflection interface interfere with each other, which makes the intensity of the terahertz wave higher. Further, such a refractive index distribution can make the ratio of the terahertz wave which propagates in the first direction 110 larger. Therefore, effect (for example, loss) of the propagation in the direction opposite to the first direction 110 on the terahertz wave can be alleviated.

Second Embodiment: Integration of Electromagnetic Wave Generating Device and Detecting Device An electromagnetic wave integrated device according to a second embodiment is now described. It should be noted that an electromagnetic wave integrated device is a device including at least an electromagnetic wave generating device and an electromagnetic wave detecting device integrated therein.

The electromagnetic wave generating device according to the first embodiment is applicable as an electromagnetic wave generating device according to this embodiment insofar as no contradiction arises.

An electromagnetic wave detecting device is a device for detecting a terahertz wave which propagates from an electromagnetic wave generating device with a carrier generated by light irradiation. A structure similar to that of the electromagnetic wave generating device according to the first embodiment is applicable as the electromagnetic wave detecting device insofar as no contradiction arises. When a terahertz wave propagates to the electromagnetic wave detecting device, a carrier is generated by light irradiation in a carrier generation layer for detection. The carrier varies depending on the intensity of the electric field of the terahertz wave. By detecting a photocurrent thereof, the intensity of the terahertz wave can be determined.

The electromagnetic wave detecting device has a first region in which a terahertz wave propagates in the first direction and a third region having an impedance which is different from an impedance of the first region and forming a reflection interface for detection with respect to a terahertz wave which propagates in the first direction.

Here, the reflection interface for detection and the third region are described with reference to FIGS. 5A to 5C for describing Example 1. First, the reflection interface for detection is a second reflection interface, and is formed so that the distance, from an irradiation location at which light is irradiated to the carrier generation layer of the electromagnetic wave generating device, to the reflection interface for detection, is smaller than D. The reflection interface for detection can be provided in the way described in the first embodiment insofar as no contradiction arises. The third region refers to a device which is on the right of the second reflection interface.

Further, the electromagnetic wave integrated device may include a propagating unit for propagating a terahertz wave generated by the electromagnetic wave generating device to the electromagnetic wave detecting device. The propagating unit has a transmission line structure similar to the structure of the electromagnetic wave generating device and the structure of the electromagnetic wave detecting device. More specifically, the propagating unit includes a plurality of electrodes and a dielectric, and a part thereof is commonly used by the electromagnetic wave generating device or the electromagnetic wave detecting device. As the dielectric, a resin material or a semiconductor material can be used. For example, such a resin material includes benzocyclobutene (BCB) which is often used as a resin material for a high-frequency wave and a polyethylene-based or polyolefin-based resin material. When a semiconductor material is used, semi-insulating silicon (SI—Si), for example, can be used. A material which is the same as the material of the carrier generation layer can also so be used. Preferably, a terahertz wave propagates through those materials with only a small loss.

The structure described above enables a terahertz wave which propagates through the transmission line to be reflected by the second reflection interface to make the intensity of the terahertz wave higher. In this way, a terahertz wave can be efficiently detected.

Third Embodiment: Electromagnetic Wave Detector

An electromagnetic wave detector according to a third embodiment is now described.

First, the electromagnetic wave detector includes an electromagnetic wave integrated device. As the electromagnetic wave integrated device, the electromagnetic wave integrated device according to the second embodiment can be used.

Next, the electromagnetic wave detector includes a light irradiation unit for irradiating light to carrier generation layers of the electromagnetic wave generating device and the electromagnetic wave detecting device.

Further, the electromagnetic wave detector includes a voltage applying unit for applying voltage to the reference electrode and the first electrode.

Still further, the electromagnetic wave detector includes a photocurrent detecting unit for detecting photocurrent of a terahertz wave which propagates to the electromagnetic wave detecting device.

The electromagnetic wave detector described above can be used in an inspection system or the like. The inspection system is described in detail in Example 7.

EXAMPLE 1

End Portion of Reference Electrode

Example 1 is now described with reference to FIGS. 5A to 5C.

FIGS. 5A and 5B are schematic views for describing an electromagnetic wave integrated device of this example. A device for generating a terahertz wave and a device for detecting a terahertz wave are integrated in a transmission line through which a terahertz wave propagates. FIG. 5C is a schematic view for describing a modification of this example.

As illustrated in FIGS. 5A-5C, the electromagnetic wave integrated device of this example includes a propagating unit 503, a first photoconductive unit 502 for generating a terahertz wave, and a second photoconductive unit 504 for detecting a terahertz wave. A photoconductive unit used herein is defined as a region from an end portion of a carrier generation layer to a reflection interface and including a portion to which excitation light is irradiated. Further, a reflection region used herein is defined as a region which is opposed to a photoconductive unit via a reflection interface. A reflection interface of this example is formed using an end portion of the reference electrode.

A terahertz wave is generated from the first photoconductive unit 502. A first reflection interface 515 reflects a terahertz wave which propagates in a direction opposite to a propagation direction 521. A first reflection region 501 is a region which includes the first reflection interface 515 and has the function of reflecting a terahertz wave. A second reflection interface 516 reflects a terahertz wave which propagates from the propagating unit 503 via the second photoconductive unit 504 again in the direction of the second photoconductive unit 504. A second reflection region 505 is a region which includes the second reflection interface 516 and has the function of reflecting a terahertz wave.

Those components are formed on a substrate 514. In this example, silicon (Si) is used as the substrate 514.

The propagating unit 503 includes a first electrode 506, a first dielectric 512, and a reference electrode 509 and forms a microstripline. In this example, the first electrode 506 is a conductor in which titanium (Ti) and gold (Au) are laminated with a thickness of 500 Å and 3000 Å, respectively, and the line width is 5 µm. The reference electrode 509 is a plate-like electrode for applying a reference potential to respective portions which form the device. Here, similarly to the case of the first electrode 506, Ti and Au are used.

Further, as the first dielectric 512, benzocyclobutene (BCB) is used. The first dielectric 512 has a film thickness of 3 µm, and the propagating unit 503 has a length of 600 µm.

In this example, the first photoconductive unit 502 and the second photoconductive unit 504 have the same structure. The first photoconductive unit 502 and the second photoconductive unit 504 include the first electrode 506 and the reference electrode 509, respectively. The first photoconductive unit 502 further includes a first carrier generation layer 510 for generating a carrier and a second electrode 507 for applying bias to the generated carrier. The second photoconductive unit 504 further includes a second carrier generation layer 511 for generating a carrier and a third electrode 508 for detecting a carrier which is changed by a terahertz wave. As the first carrier generation layer 510 and the second carrier generation layer 511, low-temperature-grown gallium arsenide (LT-GaAs) is used. The first carrier generation layer 510 and the second carrier generation layer 511 have a film thickness of 2 µm. The LT-GaAs layer is formed on a semi-insulating gallium arsenide (SI—GaAs) substrate (having a resistivity larger than $1 \times 10^7$ Ω·cm) by low temperature molecular beam epitaxial growth (at 250° C.), and is used after being peeled off from the SI—GaAs substrate. As the second electrode 507 and the third electrode 508, similarly to the above-mentioned electrodes, Au is used. The line width of those electrodes is 5 µm. Those electrodes are spaced from the first electrode 506 by 5 µm.

FIG. 5C illustrates a modification of this example. Here, as the first dielectric 512, the above-mentioned LT-GaAs layer having a film thickness of 2 µm is used. The film thicknesses of the respective carrier generation layers and the first dielectric 512 can be made the same with ease and the manufacturing process can also be simplified, whereby satisfactory propagation characteristics of the terahertz wave can also be maintained.

A bias applying unit 517 is a portion for applying bias to a gap between the first electrode 506 and the second electrode 507. In this example, an electric field of 10 V is applied to the gap by the bias applying unit 517. With this state maintained, first excitation light 519 is irradiated to the gap to generate a terahertz wave. In this example, as the first excitation light 519, an ultrashort pulse laser having a central wavelength of 800 nm, a pulse width of 50 fsec, and a pulse repetition frequency of 76 MHz from a Ti-sapphire laser generating device is used. As the light source, a small and stable fiber laser may also be used. The wavelength of the laser is adjusted to be the absorption wavelength of the carrier generating unit which is used.

Figure 7A:
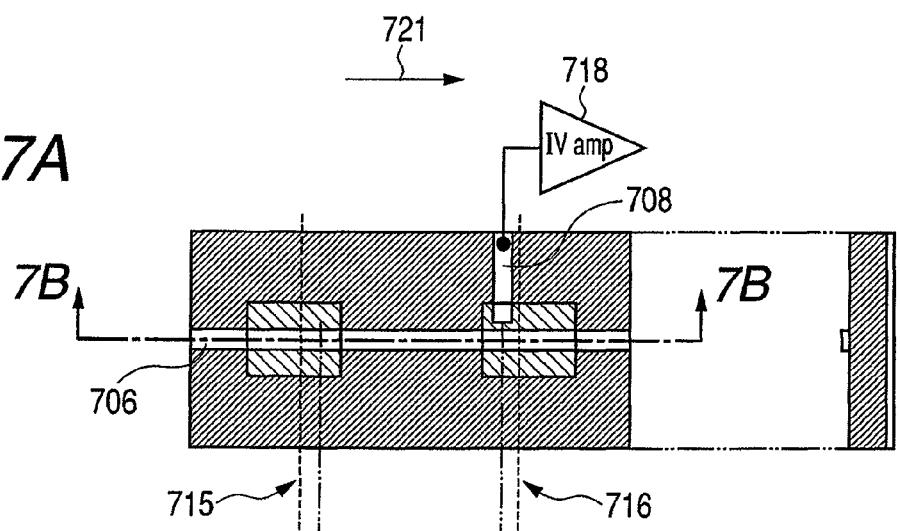
FIGS. 7A and 7B are schematic views for describing a modification of Example 1.
Figure 7B:
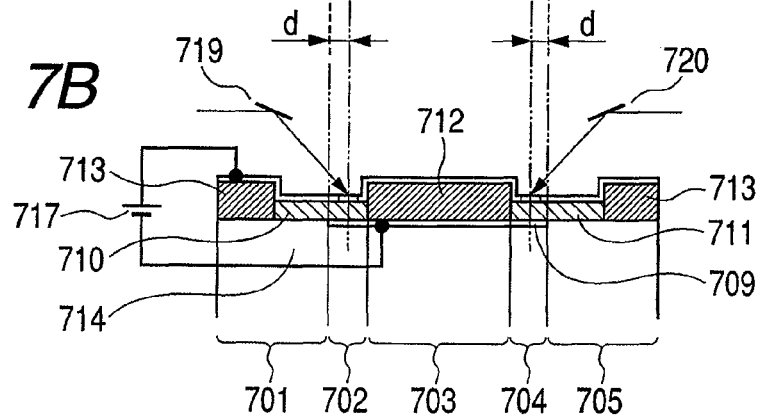

As illustrated in FIGS. 7A and 7B, bias may also be applied between a first electrode 706 and a reference electrode 709. FIGS. 7A and 7B are schematic views illustrating an exemplary method of applying bias in this case. Here, the second electrode 507 used for generating a terahertz wave is not essential. By making the bias adapted to be applied in a film thickness direction of a first carrier generation layer 710, the intensity of the electric field can be controlled through control of the film thickness. Therefore, it is easy to make the distance between the first electrode 706 and the reference electrode 709 small. As a result, it is also easy to make the intensity of the electric field applied between the electrodes high, and a more intense terahertz wave can also be generated. More specifically, the intensity of a terahertz wave is similar to a terahertz wave obtained when a terahertz wave is generated using the gap between the first electrode and the second electrode can be obtained with lower bias, and thus, power consumption of the device and of an detector including the device can be lowered. It should be noted that, in FIGS. 7A and 7B, reference numerals 701, 702, 703, 704, 705, 708, 711, 712, 713, 714, 715, 716, 717, 718, 719, 720, and 721 denote a first reflection region, a first photoconductive unit, a propagating unit, a second photoconductive unit, a second reflection region, a third electrode, a second carrier generation layer, a first dielectric, a second dielectric, a substrate, a first reflection interface, a second reflection interface, a bias applying unit, a signal detecting unit, first excitation light, second excitation light, and a propagation direction of a terahertz wave, respectively.

A signal detecting unit 518 is an unit which detects a change in carrier generated in a gap between the first electrode 506 and the third electrode 508 due to an electric field of a terahertz wave with regard to the second photoconductive unit 504. The carrier is generated by the second excitation light 520. In this example, same light is used as the first excitation light 519 and the second excitation light 520, but the irradiation timing of each excitation light is appropriately adjusted.

The first reflection region 501 is disposed at a location opposed to the first photoconductive unit 502 along the first electrode 506. More specifically, the first reflection region 501 is disposed in a direction opposite to the propagation direction 521 of a terahertz wave with respect to the first photoconductive unit 502. The second reflection region 505 is, similarly to the case of the first reflection region 501, disposed at a location opposed to the second photoconductive unit 504 along the first electrode 506. However, the second reflection region 505 is disposed on an extension of the propagation direction 521 of a terahertz wave beyond the second photoconductive unit 504.

The first reflection region 501 includes the first carrier generation layer 510 and the first electrode 506 forming the first photoconductive unit 502, and further, a second dielectric 513. The first electrode 506 included in the first reflection region 501 is used not for propagation of a terahertz wave but as a lead for mounting on a circuit (for example, bias applying unit 517) for defining a certain potential with respect to the reference electrode 509. In this example, as the second dielectric 513, SU8 which is a resist material is used. The film thickness thereof is 6 µm. As described above, because the first electrode 506 forming the first reflection region 501 is used as a lead necessary for connection to an external circuit, the material of the second dielectric 513 is not limited thereto. For example, the material of the second dielectric 513 may be the same as that of the first dielectric 512 or be a semiconductor material, or may be a material which absorbs a terahertz wave (for example, glass) consciously selected so that a terahertz wave which leaks in the first reflection region 501 is absorbed.

In this example, the structure of the second reflection region 505 is similar to that of the first reflection region 501, and hence detailed description thereof is omitted.

By making a terahertz wave reflected by the reflection interface in the reflection region and a terahertz wave which propagates in the propagation direction 521 overlap each other at the first photoconductive unit 502, the intensity of the terahertz wave is made higher. Further, a reflected terahertz wave and a terahertz wave which propagates in the propagation direction 521 are made to overlap each other at the second photoconductive unit 505 to make higher the intensity of a signal detected by the signal detecting unit 518. In this example, such a reflection interface is realized by the reference electrode 509.

The location of the first reflection interface 515 or the second reflection interface 516 is determined by the location of an end portion of the reference electrode 509 below the first carrier generation layer 510 or the second carrier generation layer 511. In this example, the location in which a terahertz wave is generated is a center location of the line width of the second electrode 507. A location d of the first reflection interface 515 is determined by a half width of a terahertz wave in the propagation direction 521 among terahertz waves generated by the first conductive unit 502. For example, in the device structure of this example, when the half width of the terahertz wave is 2 psec, the distance D converted from the half width is about 190 µm. Therefore, the location d of the reflection interface is adjusted to be the distance D or smaller. In this example, the location d of the first reflection interface 515 is 3 µm. Similarly, in this example, when the location at which a terahertz wave is detected is a center location of the line width of the third electrode 508, the location d of the second reflection interface 516 is 3 µm. Here, the location d of the reflection interface is about 0.015 D.

With such a structure, the impedance on the side of the photoconductive unit and the impedance on the side of the reflection region are discontinuous via an end portion of the reference electrode 509, and the reflection interface appears. As a modification of the reflection interface, there may be a plurality of reflection interfaces for reflecting a terahertz wave. In this case, it is desirable that a part or all of the plurality of reflection interfaces be within the effective distance converted from the half width of the terahertz wave. Also in this case, at least one reflection interface is within the effective distance, and the reflection interface forms the interface between the photoconductive unit and the reflection region.

It should be noted that, in this example, the first carrier generation layer 510 and the second carrier generation layer 511 are sandwiched between the first electrode 506 and the reference electrode 509 and divide the first dielectric 512 and the second dielectric 513, but the present invention is not limited thereto. For example, there may be another dielectric layer between the first electrode 506 and the reference electrode 509.

Figure 6A:
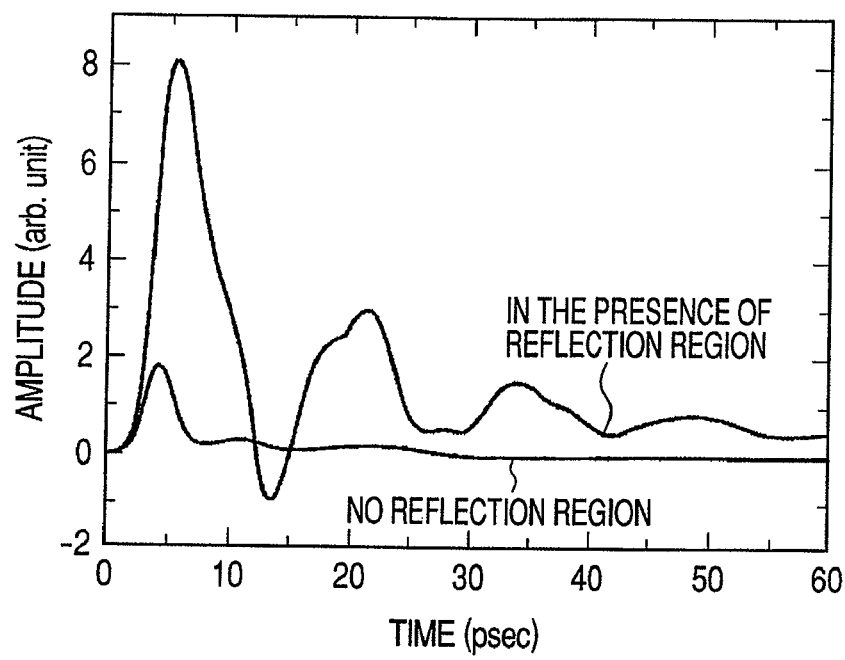
FIGS. 6A and 6B are graphs for describing an analysis result in Example 1.
Figure 6B:
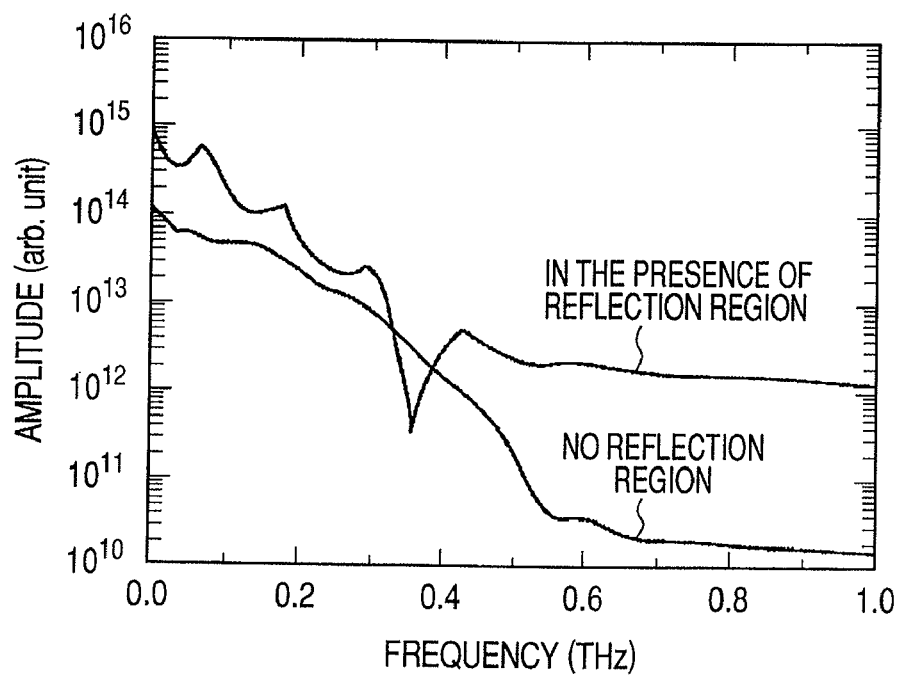

FIGS. 6A and 6B illustrate the result of electromagnetic analysis of a terahertz wave detected by the second photoconductive unit 504 with regard to the device of this example.

FIG. 6A illustrates time waveforms of terahertz waves detected by the second photoconductive unit 504. FIG. 6B illustrates frequency characteristics of terahertz waves detected by the second photoconductive unit 504. It can be seen that, in the device of this example, the peak intensity of a terahertz wave pulse is made higher and its frequency characteristics are enhanced over almost the entire wavelength range.

It should be noted that, in this example, an reflection interface is used in the first photoconductive unit 502 and the second photoconductive unit 504 to reflect a terahertz wave, but the present invention is not limited thereto. It is also possible to use a reflection interface only in one of the first photoconductive unit 502 and the second photoconductive unit 504.

With such a structure, the efficiency of using a generated terahertz wave can be improved.

EXAMPLE 2

Stub Electrode in First Electrode

Example 2 is now described with reference to FIGS. 8A to 8C.

Figure 8A:
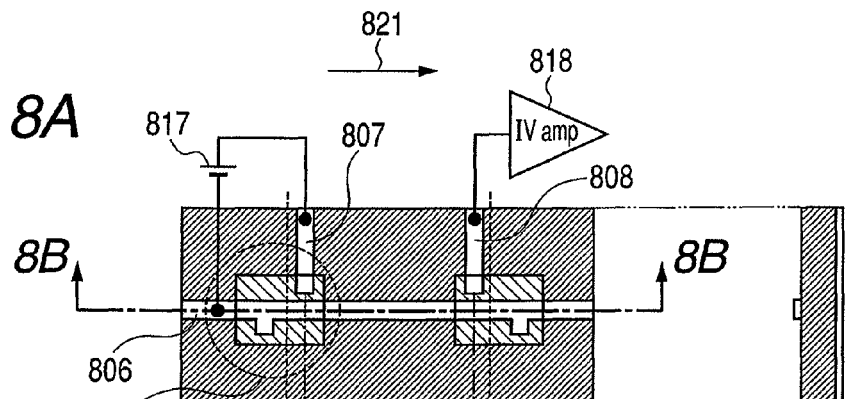
FIGS. 8A, 8B, and 8C are schematic views for describing an electromagnetic wave generating device in Example 2 of the present invention.
Figure 8B:
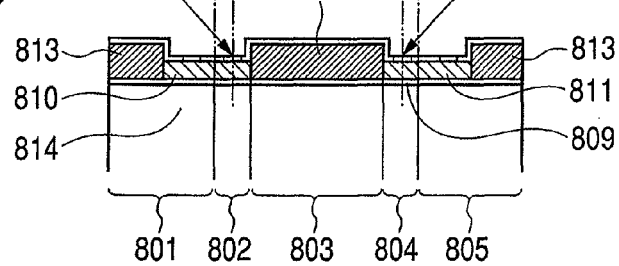
Figure 8C:
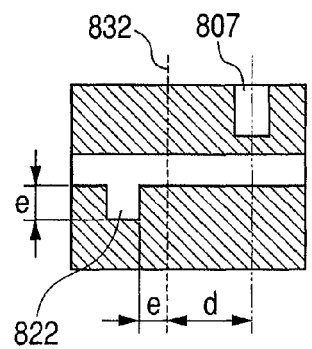

FIGS. 8A and 8B are schematic views for describing an electromagnetic wave integrated device of this example. FIG. 8C is an enlarged schematic view of a region F of FIG. 8A. Reference numerals 808, 810, 811, 812, 813, 814, 816, 817, 818, 820, and 821 denote a third electrode, a first carrier generation layer, a second carrier generation layer, a first dielectric, a second dielectric, a substrate, a second reflection interface, a bias applying unit, a signal detecting unit, second excitation light, and a propagation direction of a terahertz wave, respectively. A dotted line 832 denotes a location of a first reflection interface 815.

This example is different from Example 1 in the structure of an electrode for forming a reflection interface in a reflection region. More specifically, in order to form a reflection interface, a stub electrode 822 is used. This example is characterized in that the stub electrode 822 is used to reflect a specific terahertz wave. Further, this example is different from Example 1 in that an end portion of the reference electrode 509 is near the place at which the excitation light is irradiated in Example 1, but an end portion of a reference electrode 809 extends to a reflection region in this example.

The stub electrode 822 in a first reflection region 801 is disposed along a first electrode 806 with a specific distance (d+e) from a center of a second electrode 807 (that is, portion to which first excitation light 819 is irradiated to generate a carrier). A distance d is the distance to the first reflection interface 815. A distance e is the distance from the first reflection interface 815 to an edge of the stub electrode 822. Further, the length of the stub electrode 822 is equal to the distance e. The distance e is set to be (¼) λ when λ is the effective wavelength of a terahertz wave which is desired to be reflected. When the terahertz wave which is desired to be reflected occupies a plurality of continuous wavelength ranges, λ is the effective central wavelength of the occupied wavelength ranges.

In this way, by setting the distance from the first reflection interface 815 and the length of the stub electrode 822, at the reflection interface, with respect to a terahertz wave having a wavelength of λ, the impedance of the first reflection region 801 and the impedance of the first photoconductive unit 802 are discontinuous. More specifically, the extent of the discontinuity of the impedance is the maximum with regard to a terahertz wave having a wavelength of λ. As a result, a terahertz wave having a wavelength of λ toward the first reflection region 801 is reflected in the direction of the first photoconductive unit 802. By making the terahertz wave overlap a terahertz wave having a wavelength of λ which propagates from the first photoconductive unit 802 toward a propagating unit 803, the intensity of a terahertz wave having a wavelength of λ which propagates through the propagating unit 803 can be made higher.

Although a portion at which a terahertz wave is generated (first photoconductive unit 802) is described above, the same can be applied to a portion at which a terahertz wave is detected (second photoconductive unit 804). In other words, the efficiency of collecting a terahertz wave having a specific wavelength can also be improved.

In this example, when a location at which a terahertz wave is generated is a center location of the line width of the second electrode 807, the location d of the first reflection interface 815 is 3 μm. The length e of the stub electrode 822 in the first reflection region 801 is 50 μm. The location e of the stub electrode 822 is also 50 μm. As described above, the length and location of the stub electrode 822 correspond to ¼ of the effective wavelength λ of the reflected terahertz wave. Here, the reflected terahertz wave corresponds to about 0.5 THz. Further, the line width of the stub electrode 822 is 5 μm. A stub electrode having a similar structure is provided in a second reflection region 805.

Figure 9A:
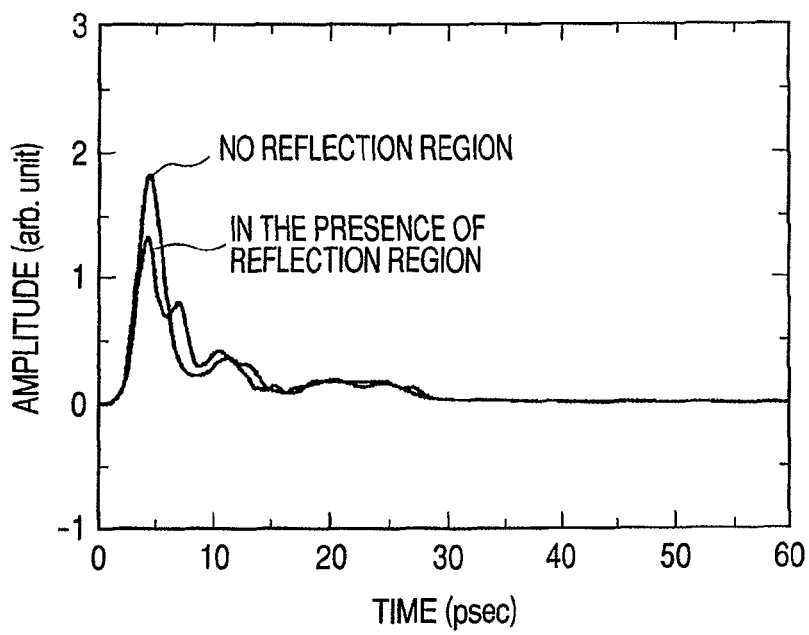
FIGS. 9A and 9B are graphs for describing an analysis result in Example 2.
Figure 9B:
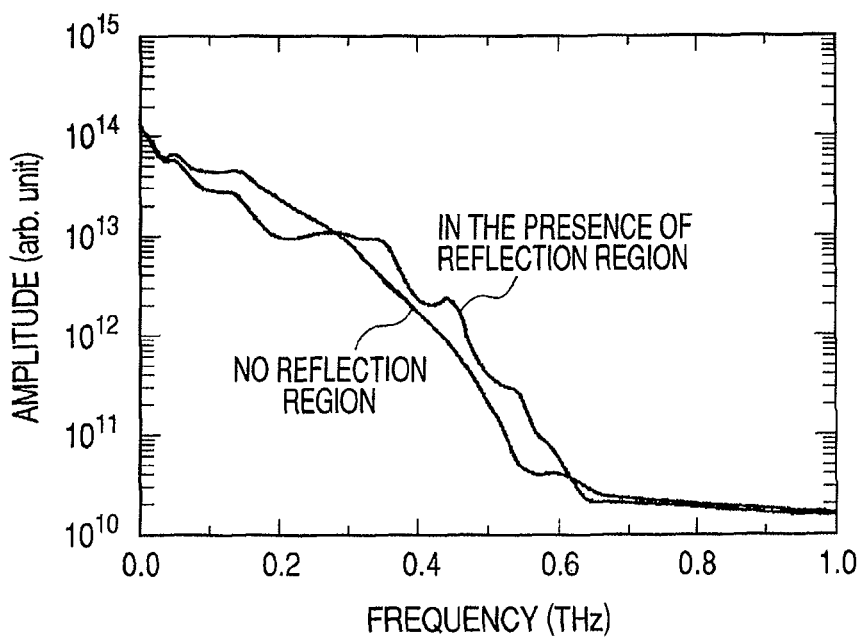

FIGS. 9A and 9B illustrate the result of electromagnetic analysis of a terahertz wave detected by the second photoconductive unit 804 with regard to the device of this example. FIG. 9A illustrates time waveforms of a terahertz wave detected by the second photoconductive unit 804. FIG. 9B illustrates frequency characteristics of a terahertz wave detected by the second photoconductive unit 804. It can be seen that the efficiency of collecting a terahertz wave is improved particularly with respect to about 0.5 THz.

Although the peak intensity of the time waveform is low, this is improved by adjusting the structure of the stub electrode. More specifically, by adjusting the line width of the electrode from the reflection interface to the stub electrode and the line width of the stub electrode itself, the wavelength range of the reflected terahertz wave can be adjusted. For example, it is thought that, by making an adjustment such that the wavelength range is extended, the ratio of wavelength which is reflected by the reflection interface and overlaps is increased, and thus, the peak intensity is improved. Extending the wavelength range is thought to be materialized by making smaller the line width of the electrode from the reflection interface to the stub electrode or by making larger the line width of the stub electrode. In some cases, the line width of the electrode from the reflection interface to the stub electrode and the line width of the stub electrode may be simultaneously adjusted. Further, the shape of the stub electrode may be adjusted to be, for example, a sector, such that desired frequency characteristics may be obtained.

Further, as a modification of this example, a plurality of stub electrodes may be used on the side of the generation or on the side of detection. For example, stub electrodes corresponding to a plurality of wavelengths are disposed along the first electrode 806. The reflection interface formed by the plurality of stub electrodes is not necessarily required to be only one. For example, as described above, insofar as the location of the reflection interface does not exceed the effective distance converted from the half width of the time waveform of a terahertz wave, the location of the reflection interface may be arbitrarily set. When there are a plurality of reflection interfaces, it is sufficient that at least the interface which is the nearest to the photoconductive unit is in this range.

In this example, the reflection region can be set by an electrode pattern on a dielectric forming the device. Therefore, the efficiency of using a generated terahertz wave can be improved more easily.

EXAMPLE 3

Uneven Width of First Electrode: Stepped Electrode

Example 3 is now described with reference to FIGS. 10A to 10C.

Figure 10A:
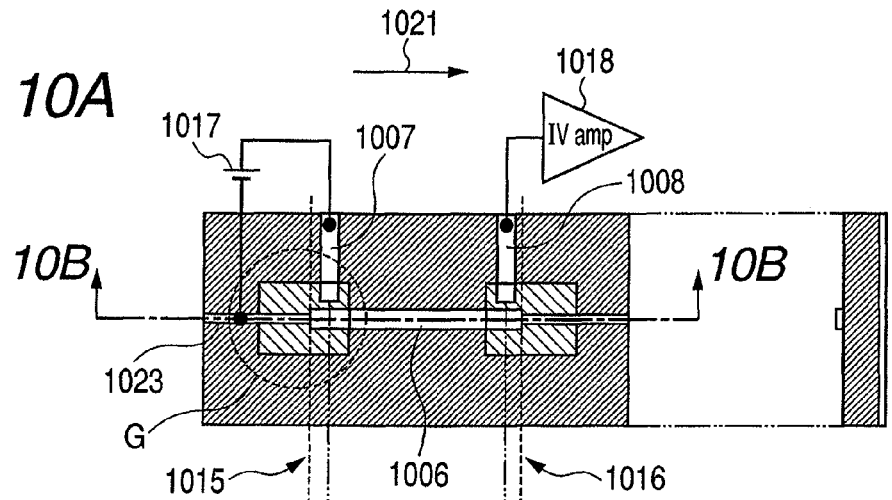
FIGS. 10A, 10B, and 10C are schematic views for describing an electromagnetic wave generating device of Example 3 of the present invention.
Figure 10B:
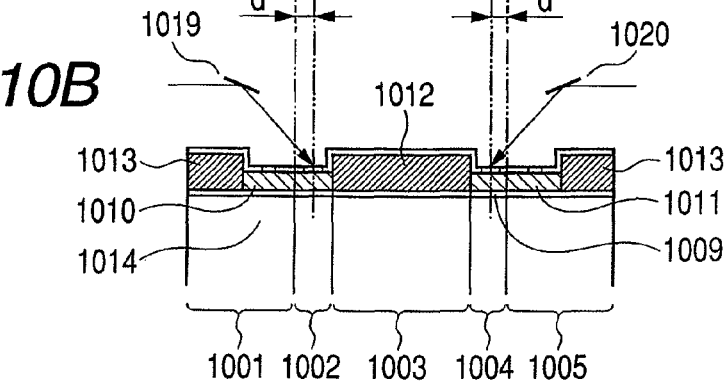
Figure 10C:
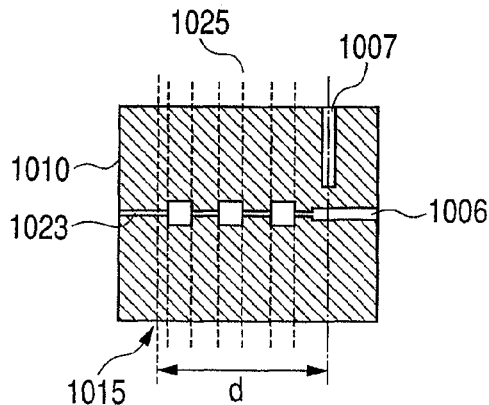

FIGS. 10A and 10B are schematic views for describing an electromagnetic wave integrated device according to this example. Reference numerals 1004, 1005, 1007, 1008, 1010, 1011, 1012, 1013, 1014, 1016, 1017, 1018, 1019, 1020, and 1021 denote a second photoconductive unit, a second reflection region, a second electrode, a third electrode, a first carrier generation layer, a second carrier generation layer, a first dielectric, a second dielectric, a substrate, a second reflection interface, a bias applying unit, a signal detecting unit, first excitation light, second excitation light, and a propagation direction of a terahertz wave, respectively. It should be noted that description of portions similar to those described above is omitted.

This example is different from the above examples in the structure of an electrode for forming a reflection interface in a reflection region. More specifically, in order to form a reflection interface, a stepped electrode 1023 is used. The stepped electrode 1023 is formed by making discontinuous the width of a first electrode 1006. Similarly to the cases of Examples 1 and 2, ends of a reference electrode 1009 extend to reflection regions.

The stepped electrode 1023 in a first reflection region 1001 is connected to a longitudinal extension of the first electrode 1006 via a first reflection interface 1015. The line width of the stepped electrode 1023 is different from the line width of the first electrode 1006. Therefore, impedance mismatch is caused via the first reflection interface 1015, and a terahertz wave toward the first reflection region 1001 is reflected in the direction of a first photoconductive unit 1002. As described above, by appropriately selecting the location of the reflection interface, the intensity of a terahertz wave which propagates through a propagating unit 1003 can be made higher.

Further, as described above, the stepped electrode 1023 is also applicable to a portion at which a terahertz wave is detected (second photoconductive unit 1004). The stepped electrode can make higher the efficiency of collecting a terahertz wave.

It should be noted that, although, in this example, a case in which there is one reflection interface is described, there may be a plurality of reflection interfaces. As illustrated in FIG. 10C, a plurality of reflection interfaces 1025 may be formed by the stepped electrode 1023. It is preferable that the plurality of reflection interfaces 1025 be within the effective distance D converted from the half width of the time waveform of a terahertz wave. However, all the interfaces are not necessarily required to be within this range, and it is sufficient that at least the interface which is the nearest to the photoconductive unit is in this range.

It is also possible to, by periodically disposing the plurality of reflection interfaces 1025, make higher the reflectivity with respect to a specific wavelength.

With such a structure, the efficiency of using a generated terahertz wave can be improved.

EXAMPLE 4

Discontinuous Distance Between First Electrode and Reference Electrode

Example 4 is now described with reference to FIG. 11.

Figure 11:
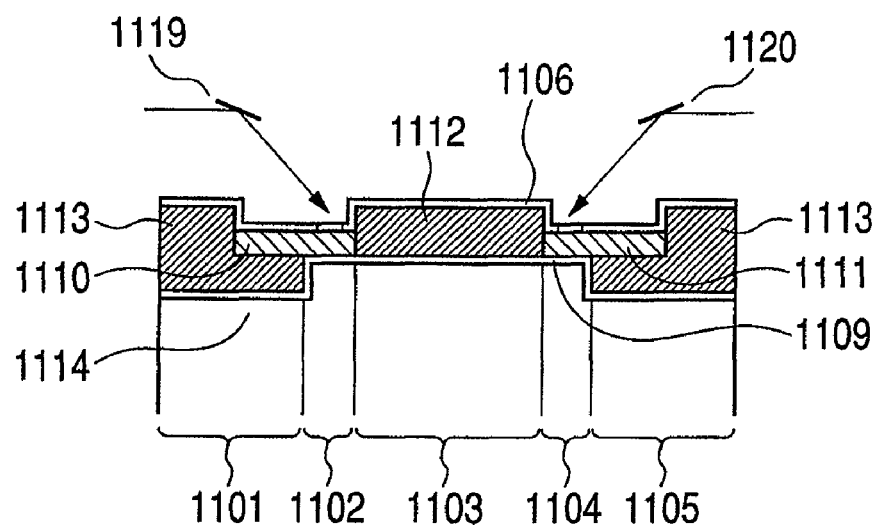
FIG. 11 is a schematic view for describing an electromagnetic wave generating device of Example 4 of the present invention.

FIG. 11 is a schematic view for describing an electromagnetic wave integrated device of this example. Reference numerals 1101, 1102, 1103, 1104, 1105, 1112, 1119, and 1120 denote a first reflection region, a first photoconductive unit, a propagating unit, a second photoconductive unit, a second reflection region, a first dielectric, first excitation light, and second excitation light, respectively. It should be noted that description of portions similar to those described above is omitted.

A reflection interface is formed by, in a carrier generation layer, making discontinuous the distance between a first electrode 1106 and a reference electrode 1109. More specifically, a dielectric layer is inserted between a region which is part of the carrier generation layer (corresponding to a carrier generation layer in a reflection region) and the reference electrode 1109.

A substrate 1114 of the device has an uneven structure. In this example, the substrate 1114 is convex, and a boundary between a convex portion and a flat portion corresponds to a reflection interface. As illustrated in FIG. 11, a second dielectric 1113 is inserted between a first carrier generation layer 1110 and a second carrier generation layer 1111 and the reference electrode 1109 which is along the shape of the substrate 1114 so as to fill the vertical gap. Such a structure changes the thickness of the dielectric forming a transmission line via the reflection interface. As a result, impedance mismatch is caused with the reflection interface being the boundary. As described above, by using such a reflection interface, the intensity of a terahertz wave which propagates and the efficiency of collecting a terahertz wave can be made higher. It should be noted that, although, in this example, there is only one convex portion, there may be a plurality of convex portions. Further, although the reflection interface is both on the side of terahertz wave generation and on the side of terahertz wave detection, the reflection interface may be only on one of the sides.

With such a structure, the efficiency of using a generated terahertz wave can be improved.

EXAMPLE 5

Vacancy in Carrier Generation Layer

Example 5 is now described with reference to FIG. 12.

Figure 12:
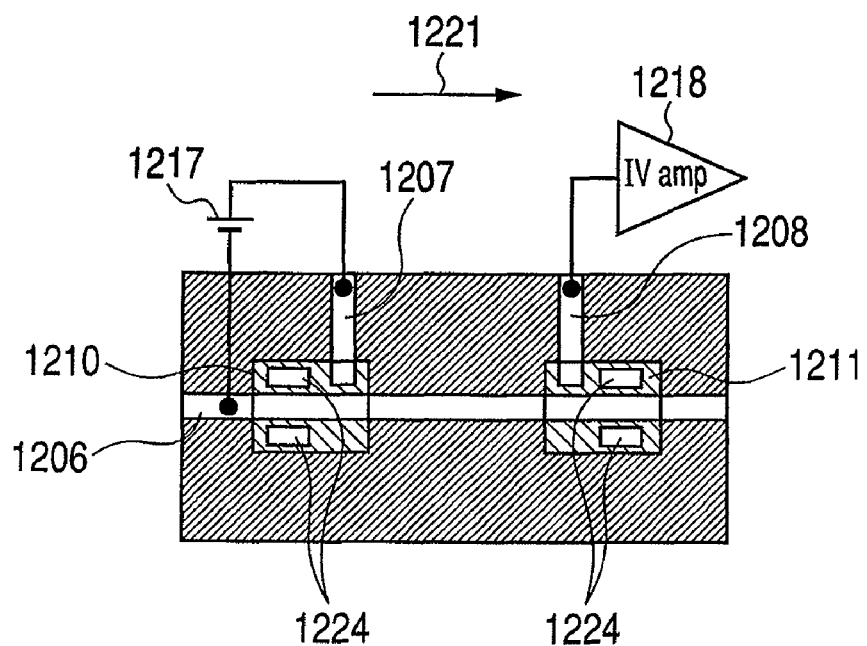
FIG. 12 is a schematic view for describing an electromagnetic wave generating device of Example 5 of the present invention.

FIG. 12 is a schematic view for describing an electromagnetic wave integrated device of this example. Reference numerals 1206, 1207, 1208, 1217, 1218, and 1221 denote a first electrode, a second electrode, a third electrode, a bias applying unit, a signal detecting unit, and a propagation direction of a terahertz wave, respectively.

In this example, another exemplary structure of a device which can carry out the present invention is described. More specifically, another structure of a reflection region is described. It should be noted that description of portions similar to those described above is omitted.

This example is different from other examples in the structure of a carrier generation layer for forming a reflection interface in a reflection region. More specifically, part of a region of the carrier generation layer has a vacancy 1224.

The vacancy 1224 changes the effective refractive index of the carrier generation layer. For example, the vacancy 1224 changes the refractive index of the carrier generation layer which forms a photoconductive unit and a reflection region with the reflection interface being the boundary. As a result, impedance mismatch is caused with the reflection interface being the boundary. By using such a reflection interface, the intensity of a terahertz wave which propagates and the efficiency of collecting a terahertz wave can be made higher. It should be noted that, although, in this example, the vacancy 1224 is provided both in a first carrier generation layer 1210 and a second carrier generation layer 1211, the vacancy 1224 may be provided only in one of the carrier generation layers. Further, the vacancy 1224 may be filled with another dielectric material. Still further, a plurality of the vacancy 1224 may be periodically disposed.

With such a structure, the efficiency of using a generated terahertz wave can be improved.

EXAMPLE 6

End of First Electrode

Example 6 is now described with reference to FIGS. 13A and 13B.

Figure 13A:
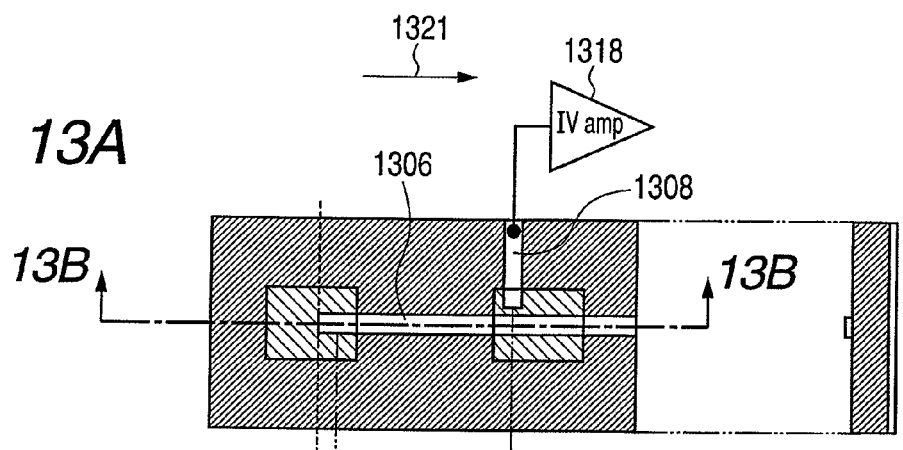
FIGS. 13A and 13B are schematic views for describing an electromagnetic wave generating device of Example 6 of the present invention.
Figure 13B:
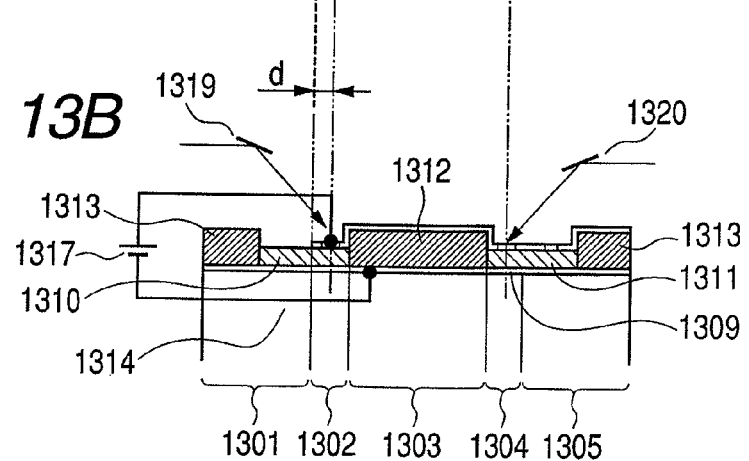

FIGS. 13A and 13B are schematic views for describing an electromagnetic wave integrated device of this example. Reference numerals 1305, 1308, 1310, 1311, 1312, 1313, 1314, 1318, 1319, 1320, and 1321 denote a second reflection region, a third electrode, a first carrier generation layer, a second carrier generation layer, a first dielectric, a second dielectric, a substrate, a signal detecting unit, first excitation light, second excitation light, and a propagation direction of a terahertz wave, respectively.

In this example, another exemplary structure of a device which can carry out the present invention is described. More specifically, another structure of a reflection region is described. It should be noted that description of portions similar to those described above is omitted.

This example is different from other examples in the structure of an electrode for forming a reflection interface in a reflection region. More specifically, in order to form the reflection interface, an end of a first electrode 1306 is adjusted to be at the location of a first reflection interface 1315. Further, ends of a reference electrode 1309 extend to reflection regions. A bias applying unit 1317 is adapted to apply bias between the first electrode 1306 and the reference electrode 1309.

In such a structure, impedance mismatch is caused via the end of the first electrode 1306 at the location of the first reflection interface 1315, and a terahertz wave toward a first reflection region 1301 is reflected in the direction of a first photoconductive unit 1302. By appropriately selecting the location of the reflection interface, the intensity of a terahertz wave which propagates through a propagating unit 1303 can be made higher.

It should be noted that, although a portion at which a terahertz wave is detected (second photoconductive unit 1304) is not adapted to have the reflection interface formed therein, it is also possible to provide a reflection interface therein similarly to the case of the above examples. With such a structure, the efficiency of collecting a terahertz wave can be made higher.

With such a structure, the efficiency of using a generated terahertz wave can be improved.

EXAMPLE 7

Inspection System

Example 7 is now described with reference to FIG. 19.

In this example, an electromagnetic wave detector is used in an inspection system for inspecting a sample.

Here, the electromagnetic wave detector has the following structure.

First, the electromagnetic wave detector has a light irradiation means for irradiating light to carrier generation layers of an electromagnetic wave generating device and an electromagnetic wave detecting device.

Second, the electromagnetic wave detector has a voltage applying means for applying voltage to a reference electrode and a first electrode.

Further, the electromagnetic wave detector has a photocurrent detecting means for detecting photocurrent of a terahertz wave which propagates to the electromagnetic wave detecting device.

Figure 19:
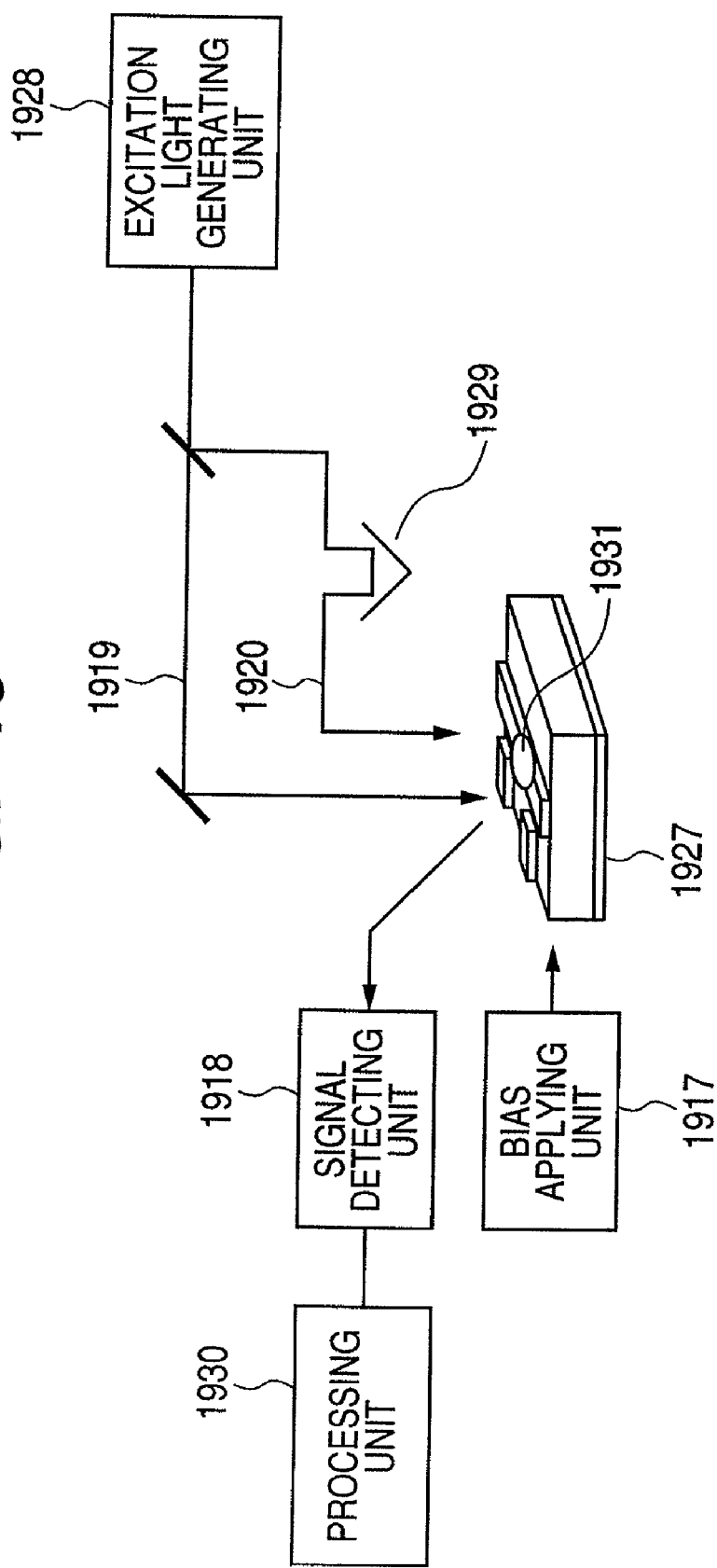
FIG. 19 is a schematic view for describing an inspection system.
Figure 20:
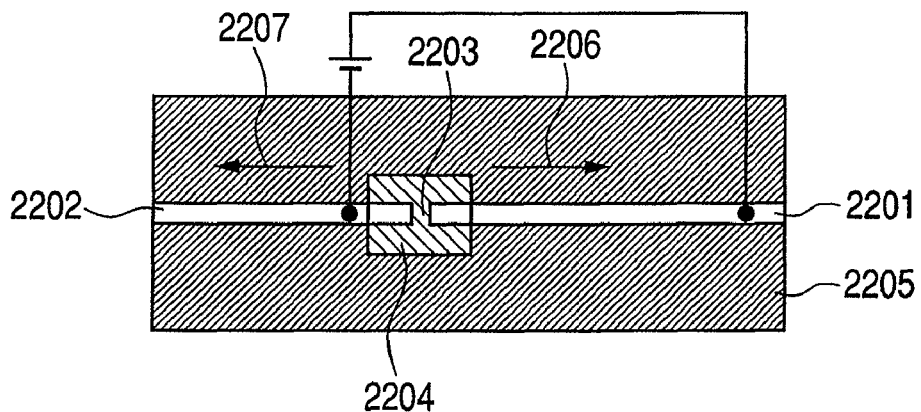
FIG. 20 is a schematic view for describing the related art.

FIG. 19 illustrates an exemplary structure of the electromagnetic wave integrated device of the above examples, which is applied to an inspection system as an inspecting device 1927 for inspecting a sample 1931.

The inspecting device 1927 has a portion at which a terahertz wave is generated and a portion at which a terahertz wave is detected, each of which is integrated in a transmission line. The inspecting device 1927 has the reflection region in at least one of a terahertz wave generating device and a terahertz wave detecting device. The inspecting device 1927 with the reflection region has the function of making higher the intensity of a terahertz wave which propagates through the transmission line or of making higher the efficiency of collecting a terahertz wave when detected.

The sample 1931 is held on the transmission line.

This example has a bias applying unit 1917 as the voltage applying means for applying voltage to the reference electrode and the first electrode. The bias applying unit 1917 is a portion which applies bias to a photoconductive unit located at a portion which generates a terahertz wave.

Further, this example has a signal detecting unit 1918 as the photocurrent detecting means for detecting photocurrent of a terahertz wave which propagates to the electromagnetic wave detecting device. The signal detecting unit 1918 is a portion which detects from a photoconductive unit located at a portion which detects a terahertz wave a current signal corresponding to the intensity of the terahertz wave.

Still further, in this example, there is provided an excitation light generating unit 1928 as the light irradiation means for irradiating light to the carrier generation layers of the electromagnetic wave generating device and the electromagnetic wave detecting device. Although the structure is so made that excitation light generated from the excitation light generating unit 1928 is branched into first excitation light 1919 and second excitation light 1920, the present invention is not limited thereto. Here, the first excitation light 1919 is used for generating a terahertz wave while the second excitation light 1920 is used for detecting a terahertz wave. An optical delay unit 1929 is a portion which adjusts the timing at which the first excitation light 1919 reaches the inspecting device 1927 and the timing at which the second excitation light 1920 reaches the inspecting device 1927.

For example, in a processing unit 1930, by plotting output of the signal detecting unit 1918 with the timings being adjusted, a time waveform of a terahertz wave which propagates on the inspecting device 1927 is obtained. The state of the sample 1931 is inspected through change in the time waveform.

EXAMPLE 8

Example 8 illustrates another exemplary structure of a device which can carry out the present invention. More specifically, Example 8 illustrates a structure of a line forming the device. It should be noted that description of portions similar to those described above is omitted.

This example is different from other examples described above with a structure using a microstripline in which a dielectric is sandwiched between two electrodes in that a structure of another transmission line is used.

Figure 14A:
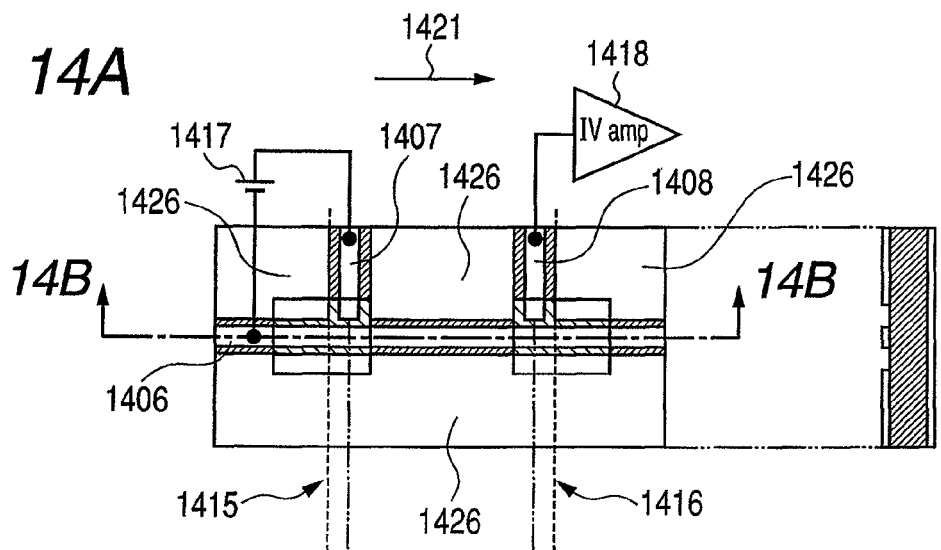
FIGS. 14A and 14B are schematic views for describing a modification of Example 1.
Figure 14B:
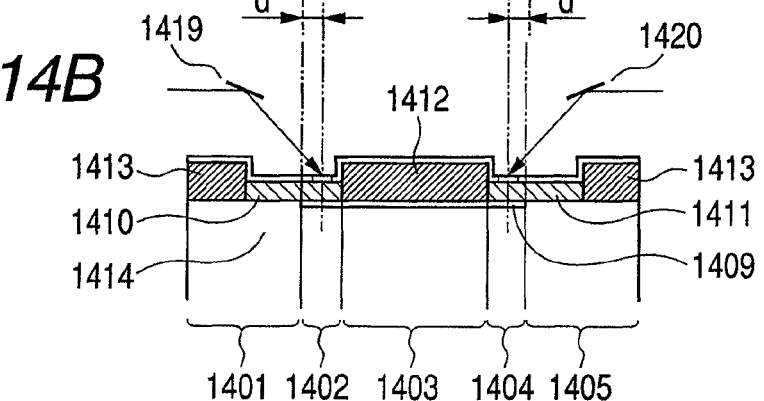

FIGS. 14A and 14B illustrate a device structure in which the locations of reflection interfaces are determined by ends of a first reference electrode 1409 formed on a substrate 1414. The present device has, in addition to the device structure used in the examples described above, a plurality of second reference electrodes 1426 disposed on a surface on which a first electrode 1406 is formed, with a certain space between the first electrode 1406 and the second reference electrodes 1426. Such a transmission line is referred to as a grounded coplanar waveguide. The reflection interfaces are formed by the first reference electrode 1409 formed on the substrate 1414. It should be noted that reference numerals 1401, 1402, 1403, 1404, 1405, 1407, 1408, 1410, 1411, 1412, 1413, 1415, 1416, 1417, 1418, 1419, 1420, and 1421 denote a first reflection region, a first photoconductive unit, a propagating unit, a second photoconductive unit, a second reflection region, a second electrode, a third electrode, a first carrier generation layer, a second carrier generation layer, a first dielectric, a second dielectric, a first reflection interface, a second reflection interface, a bias applying unit, a signal detecting unit, first excitation light, second excitation light, and a propagation direction of a terahertz wave, respectively.

FIGS. 15A and 15B and FIGS. 16A and 16B illustrate modifications of the device illustrated in FIGS. 14A and 14B. Reference numerals 1501, 1502, 1503, 1504, 1505, 1507, 1508, 1509, 1510, 1511, 1512, 1513, 1514, 1515, 1516, 1517, 1518, 1519, 1520, and 1521 denote a first reflection region, a first photoconductive unit, a propagating unit, a second photoconductive unit, a second reflection region, a second electrode, a third electrode, a first reference electrode, a first carrier generation layer, a second carrier generation layer, a first dielectric, a second dielectric, a substrate, a first reflection interface, a second reflection interface, a bias applying unit, a signal detecting unit, first excitation light, second excitation light, and a propagation direction of a terahertz wave, respectively. It should also be noted that reference numerals 1601, 1602, 1603, 1604, 1605, 1607, 1608, 1610, 1611, 1612, 1613, 1615, 1616, 1617, 1618, 1619, 1620, and 1621 denote a first reflection region, a first photoconductive unit, a propagating unit, a second photoconductive unit, a second reflection region, a second electrode, a third electrode, a first carrier generation layer, a second carrier generation layer, a first dielectric, a second dielectric, a first reflection interface, a second reflection interface, a bias applying unit, a signal detecting unit, first excitation light, second excitation light, and a propagation direction of a terahertz wave, respectively.

Figure 15A:
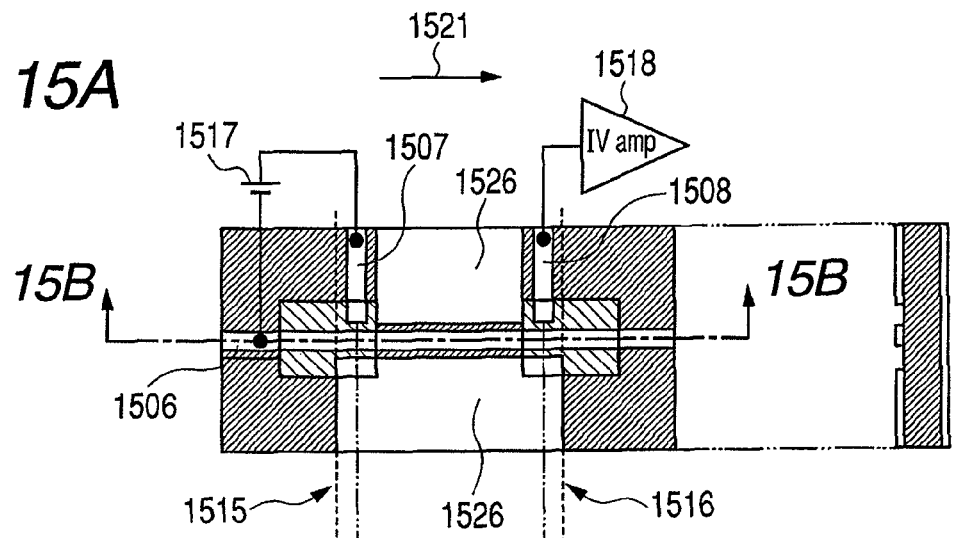
FIGS. 15A and 15B are schematic views for describing another modification of Example 1.
Figure 15B:
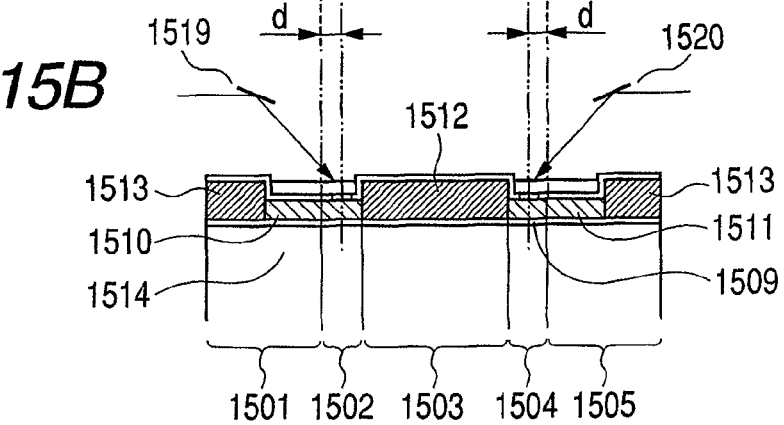

In the device illustrated in FIGS. 15A and 15B, reflection interfaces are formed by ends of a plurality of second reference electrodes 1526 which are on the same surface as a first electrode 1506.

In the device illustrated in FIGS. 16A and 16B, reflection interfaces are formed by a first reference electrode 1609 formed on a substrate 1614 and a plurality of second reference electrodes 1626 which are on the same surface as a first electrode 1606.

Figure 17A:
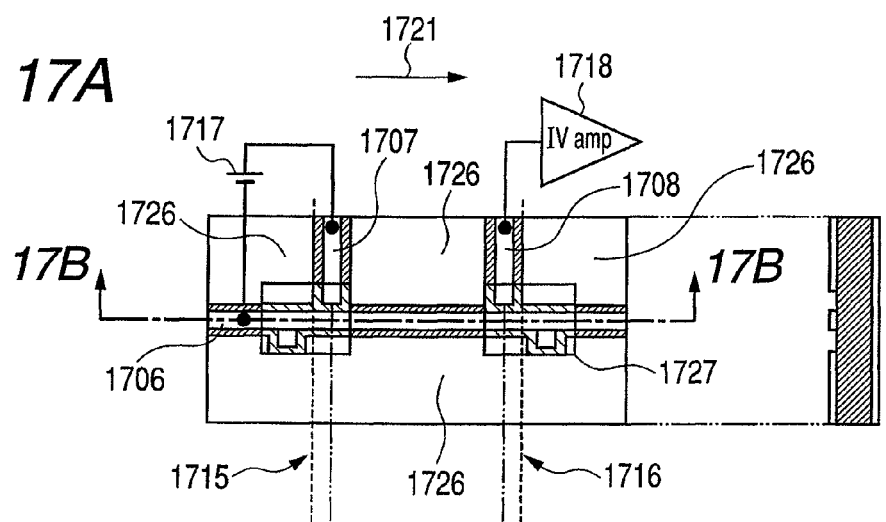
FIGS. 17A and 17B are schematic views for describing a modification of Example 2.
Figure 17B:
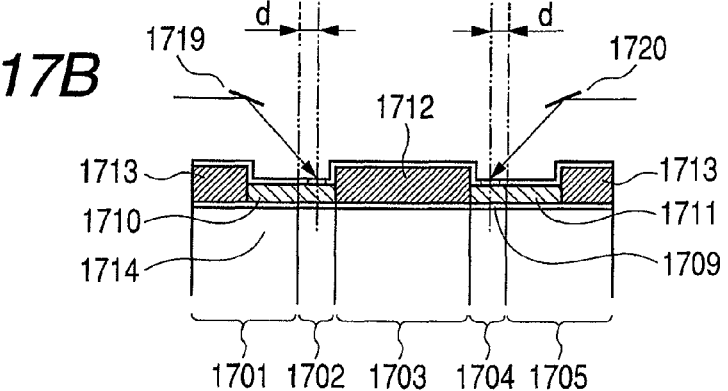

A device illustrated in FIGS. 17A and 17B is a device in which a grounded coplanar waveguide is applied as a transmission line and which determines the location of a reflection interface by a stub electrode 1727. Second reference electrodes 1726 are disposed with a certain space between the stub electrode 1727 and the second reference electrodes 1726. Here, frequency characteristics of a terahertz wave to be reflected are determined by the line width of an electrode which reaches the stub electrode 1727 and the line width of the stub electrode itself. The characteristics can be adjusted by the space between the stub electrode 1727 and the second reference electrodes 1726. It should be noted that reference numerals 1701, 1702, 1703, 1704, 1705, 1706, 1707, 1708, 1709, 1710, 1711, 1712, 1713, 1714, 1715, 1716, 1717, 1718, 1719, 1720, and 1721 denote a first reflection region, a first photoconductive unit, a propagating unit, a second photoconductive unit, a second reflection region, a first electrode, a second electrode, a third electrode, a first reference electrode, a first carrier generation layer, a second carrier generation layer, a first dielectric, a second dielectric, a substrate, a first reflection interface, a second reflection interface, a bias applying unit, a signal detecting unit, first excitation light, second excitation light, and a propagation direction of a terahertz wave, respectively.

Figure 18A:
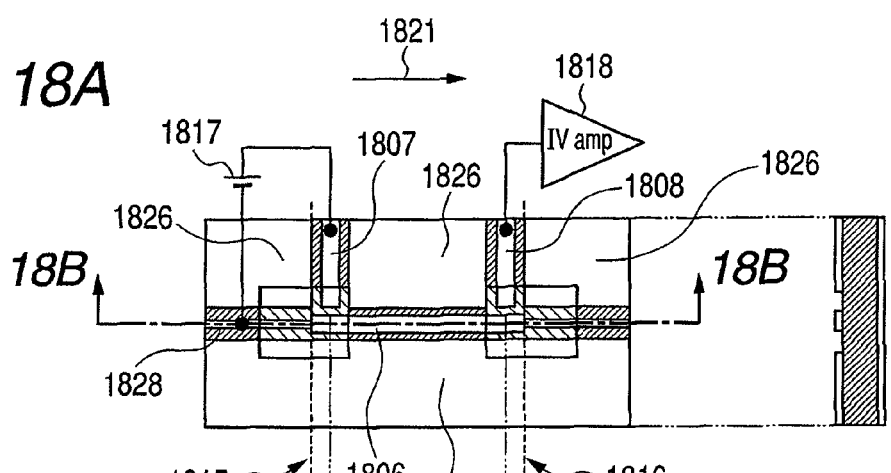
FIGS. 18A and 18B are schematic views for describing a modification of Example 3.
Figure 18B:
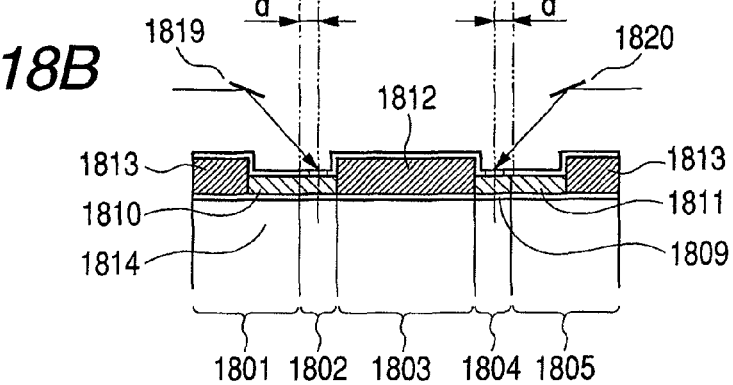

Further, a device illustrated in FIGS. 18A and 18B is a device in which a grounded coplanar waveguide is applied as a transmission line and which determines the location of a reflection interface by a stepped electrode 1828. Second reference electrodes 1826 are disposed with a certain space between the stepped electrode 1828 and the second reference electrodes 1826. Here, characteristics of a terahertz wave to be reflected are determined by the line width of the stepped electrode. The characteristics can be adjusted by the space between the stepped electrode 1828 and the second reference electrodes 1826. It should be noted that reference numerals 1801, 1802, 1803, 1804, 1805, 1806, 1807, 1808, 1809, 1810, 1811, 1812, 1813, 1814, 1815, 1816, 1817, 1818, 1819, 1820, and 1821 denote a first reflection region, a first photoconductive unit, a propagating unit, a second photoconductive unit, a second reflection region, a first electrode, a second electrode, a third electrode, a first reference electrode, a first carrier generation layer, a second carrier generation layer, a first dielectric, a second dielectric, a substrate, a first reflection interface, a second reflection interface, a bias applying unit, a signal detecting unit, first excitation light, second excitation light, and a propagation direction of a terahertz wave, respectively.

With such a structure, the efficiency of using a generated terahertz wave can be improved.

A device in which structures and ideas described in the above examples are appropriately combined is provided. Other device structures are also possible which fall within the scope of the present invention.

One device can perform the function of an electromagnetic wave generating device and the function of an electromagnetic wave detecting device. For example, by switching between a portion which applies bias to the device and a portion which obtains current generated by a terahertz wave using timings of light irradiated to the device, a device which generates and detects an electromagnetic wave can be formed.

EXAMPLE 9

End of Reference Electrode of Example 1

Example 9 is now described with reference to FIGS. 5A to 5C. FIGS. 5A and 5B are schematic views for describing an electromagnetic wave integrated device of this example. A device for generating a terahertz wave and a device for detecting a terahertz wave are integrated in a transmission line through which a terahertz wave propagates. In this example, the value of the location d of the reflection interface is different from that in Example 1. It should be noted that description of portions similar to those described in Example 1 is omitted.

In this example, the location d of the first reflection interface 515 is 170 μm. Similarly, the location d of the second reflection interface 516 is 170 μm. Here, the location d of the reflection interfaces is about 0.9 D.

Figure 21:
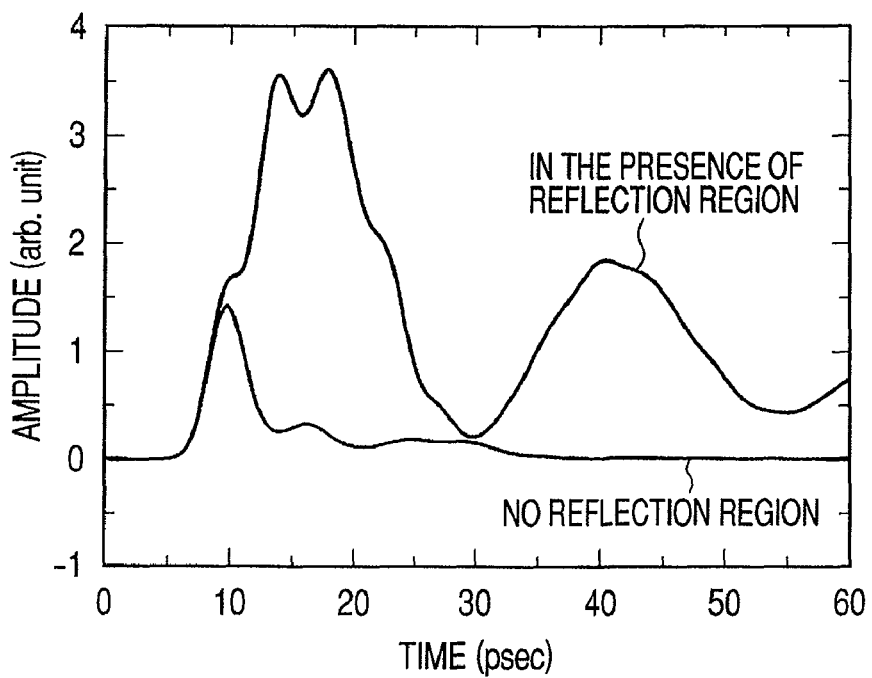
FIG. 21 is a graph for describing an analysis result in Example 9.

FIG. 21 illustrates the result of electromagnetic analysis of a terahertz wave detected by the second photoconductive unit 504 with regard to the device of this example. It can be seen that, from FIG. 21, when the location d of the reflection interface is smaller than D, the peak intensity of a terahertz wave pulse can be increased.

With such a structure, the efficiency of using a generated terahertz wave can be improved.

EXAMPLE 10

End of Reference Electrode of Example 1

Example 10 is now described with reference to FIGS. 5A to 5C. FIGS. 5A and 5B are schematic views for describing an electromagnetic wave integrated device of this example. A device for generating a terahertz wave and a device for detecting a terahertz wave are integrated in a transmission line through which a terahertz wave propagates. In this example, the value of the location d of the reflection interface is different from that in Example 1. It should be noted that description of portions similar to those described in Example 1 is omitted.

In this example, the location d of the first reflection interface 515 is 80 μm. Similarly, the location d of the second reflection interface 516 is 80 μm. Here, the location d of the reflection interfaces is about 0.42 D.

Figure 22:
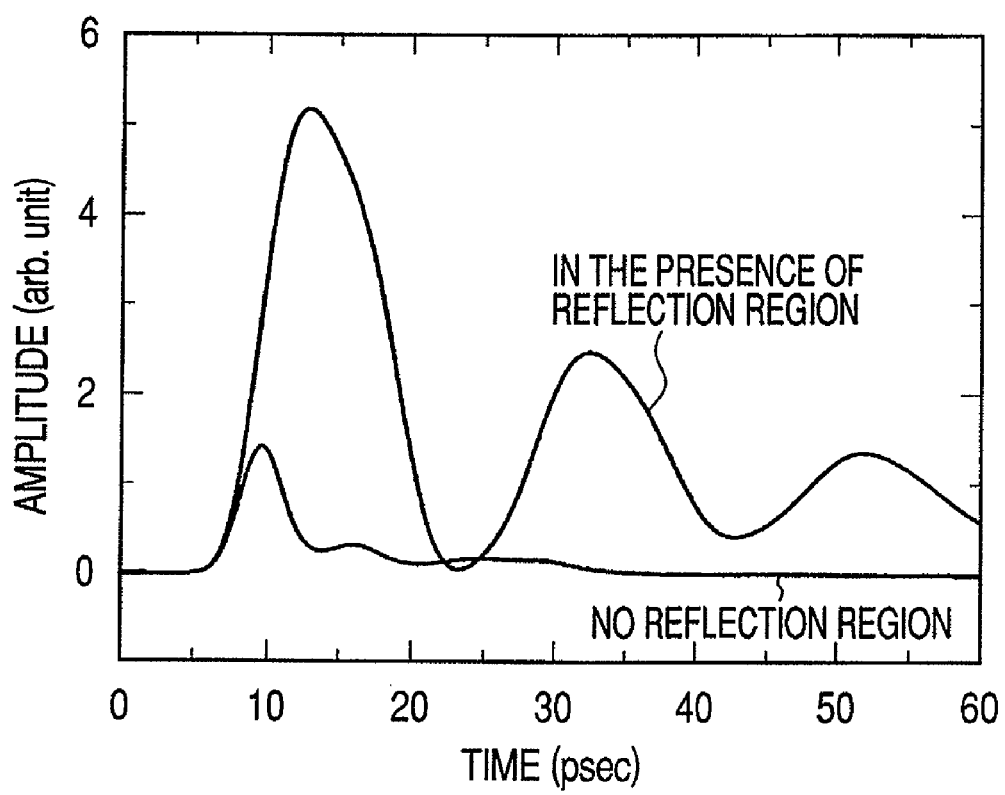
FIG. 22 is a graph for describing an analysis result in Example 10.

FIG. 22 illustrates the result of electromagnetic analysis of a terahertz wave detected by the second photoconductive unit 504 with regard to the device of this example. It can be seen that, from FIG. 22, when the location d of the reflection interface is 0.5 D or smaller, the peak intensity of a terahertz wave pulse is increased, and still, the terahertz wave which propagates does not split.

With such a structure, the efficiency of using a generated terahertz wave can be improved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-316807, filed Dec. 7, 2007, which is hereby incorporated by reference herein in its entirety.

What is claimed is:

1. An electromagnetic wave generating device, comprising:
   a carrier generation layer for generating a carrier by light irradiation;
   a first electrode provided on the carrier generation layer for applying voltage to the carrier generation layer;
   a reference electrode provided on the carrier generation layer for defining a reference potential of the first electrode; and
   a transmission line for propagating a terahertz wave generated based on the carrier generated in the carrier generation layer, the transmission line being formed so as to include the first electrode, wherein:
   the transmission line includes:
      a first region in which the terahertz wave propagates in a first direction; and
      a second region having an impedance different from an impedance of the first region and forming a reflection interface with respect to a terahertz wave which propagates in a direction opposite to the first direction; and
   a distance from an irradiation location at which light is irradiated to the carrier generation layer to the reflection interface is set to be smaller than D, where D is a distance converted from a half width of a time waveform of the terahertz wave which propagates in the first direction without passing through the reflection interface.

2. An electromagnetic wave generating device according to claim 1, wherein the distance from the irradiation location to the reflection interface is 0.5 D or smaller.

3. An electromagnetic wave generating device according to claim 1, wherein a refractive index of the first region is larger than a refractive index of the second region.

4. An electromagnetic wave generating device according to claim 1, wherein the reflection interface is formed using at least one of an end portion of the reference electrode and an end portion of the first electrode.

5. An electromagnetic wave generating device according to claim 1, wherein:
   the reflection interface formed so that the distance from the irradiation location at which light is irradiated to the carrier generation layer is set to be smaller than D is formed by a stub electrode provided at the first electrode; and
   the stub electrode is disposed at a location away from the reflection interface in a direction opposite to the first direction by ¼ of an effective wavelength of the terahertz wave which propagates in the direction opposite to the first direction, and the length of the stub electrode is ¼ of the wavelength.

6. An electromagnetic wave generating device according to claim 1, wherein the reflection interface is formed by making a width of the first electrode discontinuous.

7. An electromagnetic wave generating device according to claim 1, wherein the reflection interface is formed by, in the carrier generation layer, making the distance between the reference electrode and the first electrode discontinuous.

8. An electromagnetic wave generating device according to claim 1, wherein the reflection interface is formed by providing in the carrier generation layer a material having a refractive index different from a refractive index of the carrier generation layer.

9. An electromagnetic wave generating device according to claim 1, wherein:
   the first electrode is provided on a first surface of the carrier generation layer; and
   the reference electrode is provided on a second surface opposed to the first surface of the carrier generation layer.

10. An electromagnetic wave integrated device, comprising:

the electromagnetic wave generating device according to claim 1 and;

an electromagnetic wave detecting device for detecting a terahertz wave with a carrier generated by light irradiation, wherein:

the electromagnetic wave integrated device includes:

a first region in which the terahertz wave propagates in a first direction; and a third region having an impedance different from an impedance of the first region and forming a reflection interface for detection with respect to a terahertz wave which propagates in the first direction; and a distance from an irradiation location at which light is irradiated to the carrier generation layer of the electromagnetic wave generating device to the reflection interface for detection is set to be smaller than D.

11. An electromagnetic wave detector, comprising:

the electromagnetic wave integrated device according to claim 10;

light irradiation means for irradiating light to a carrier generation layer of the electromagnetic wave generating device and a carrier generation layer of the electromagnetic wave detecting device;

voltage applying means for applying voltage to the reference electrode and the first electrode; and photocurrent detecting means for detecting photocurrent of a terahertz wave which propagates to the electromagnetic wave detecting device.

12. An electromagnetic wave generating device, comprising:

a carrier generation layer for generating a carrier by light irradiation;

a first electrode provided on a first surface of the carrier generation layer for applying voltage to the carrier generation layer;

a reference electrode provided on a second surface opposed to the first surface of the carrier generation layer for defining a reference potential of the first electrode; and a transmission line for propagating a terahertz wave generated based on the carrier generated in the carrier generation layer, the transmission line being formed so as to include the first electrode, wherein:

the transmission line includes:

a first region in which the terahertz wave propagates in a first direction; and a second region having an impedance different from an impedance of the first region and forming a reflection interface with respect to a terahertz wave which propagates in a direction opposite to the first direction;

a distance from an irradiation location at which light is irradiated to the carrier generation layer to the reflection interface is set to be equal to or smaller than 0.5 D, where D is a distance converted from a half width of a time waveform of a terahertz wave which propagates in the first direction without passing through the reflection interface; and a refractive index of the first region is larger than a refractive index of the second region.

\* \* \* \* \*